(12) United States Patent
McGuckin, Jr. et al.

(10) Patent No.: US 8,128,653 B2
(45) Date of Patent: Mar. 6, 2012

(54) VASCULAR HOLE CLOSURE DEVICE

(75) Inventors: James F. McGuckin, Jr., Radnor, PA (US); Richard T. Briganti, Malvern, PA (US)

(73) Assignee: Rex Medical, L.P., Conshohocken, PA (US)

( * ) Notice: Subject to any disclaimer, the term of this patent is extended or adjusted under 35 U.S.C. 154(b) by 1234 days.

(21) Appl. No.: 11/893,949

(22) Filed: Aug. 17, 2007

(65) Prior Publication Data

US 2007/0293880 A1     Dec. 20, 2007

Related U.S. Application Data

(63) Continuation of application No. 10/345,533, filed on Jan. 16, 2003, now Pat. No. 7,267,679, which is a continuation-in-part of application No. 10/163,142, filed on Jun. 5, 2002, now Pat. No. 7,341,595, application No. 11/893,949, which is a continuation-in-part of application No. 10/846,801, filed on May 14, 2004, now Pat. No. 7,662,168, which is a continuation of application No. 10/269,899, filed on Oct. 11, 2002, now Pat. No. 6,749,622, which is a continuation of application No. 09/659,648, filed on Sep. 12, 2000, now abandoned.

(60) Provisional application No. 60/355,526, filed on Feb. 6, 2002, provisional application No. 60/153,736, filed on Sep. 13, 1999.

(51) Int. Cl.
*A61B 17/08*     (2006.01)
*A61D 1/00*     (2006.01)

(52) U.S. Cl. ...................................... 606/213; 606/151

(58) Field of Classification Search ................ 606/151, 606/213, 215, 219–221
See application file for complete search history.

(56) References Cited

U.S. PATENT DOCUMENTS

| | | |
|---|---|---|
| 2,024,871 A | 12/1935 | Parsons |
| 2,398,220 A | 4/1946 | Gelpcke |
| 3,527,223 A | 9/1970 | Melvin |
| 3,874,388 A | 4/1975 | King et al. |
| 3,937,217 A | 2/1976 | Kosonen |
| 3,958,576 A | 5/1976 | Komiya |
| 4,007,743 A | 2/1977 | Blake |
| 4,031,569 A | 6/1977 | Jacob |
| 4,117,838 A | 10/1978 | Hasson |
| 4,286,497 A | 9/1981 | Shamah |
| 4,317,445 A | 3/1982 | Robinson |
| 4,485,816 A | 12/1984 | Krumme |
| 4,505,274 A | 3/1985 | Speelman |
| 4,512,338 A | 4/1985 | Balko et al. |
| 4,610,671 A | 9/1986 | Luther |

(Continued)

FOREIGN PATENT DOCUMENTS

DE     19604817     8/1997

(Continued)

*Primary Examiner* — Corrine M McDermott
*Assistant Examiner* — Dianne Dornbusch
(74) *Attorney, Agent, or Firm* — Neil D. Gershon

(57) ABSTRACT

A device for closing an aperture in a vessel wall comprising an elongated member positionable inside the vessel against an internal opening of the aperture and having a dimension exceeding a dimension of the internal opening of the aperture to prevent egress of fluid through the aperture. At least two curved legs are coupled to the elongated member, curve in a direction substantially perpendicular to the longitudinal axis of the elongated member, and are positionable outside the vessel to help retain the elongated member in position the legs.

20 Claims, 38 Drawing Sheets

U.S. PATENT DOCUMENTS

| | | | |
|---|---|---|---|
| 4,615,514 A | 10/1986 | Hamlin | |
| 4,638,803 A | 1/1987 | Rand | |
| 4,665,906 A | 5/1987 | Jervis | |
| 4,676,245 A | 6/1987 | Fukuda | |
| 4,744,364 A | 5/1988 | Kensey | |
| 4,836,204 A | 6/1989 | Landymore et al. | |
| 4,917,089 A | 4/1990 | Sideris | |
| 4,924,866 A | 5/1990 | Yoon | |
| 4,971,068 A | 11/1990 | Sahi | |
| 5,021,059 A | 6/1991 | Kensey et al. | |
| 5,047,047 A | 9/1991 | Yoon | |
| 5,061,274 A | 10/1991 | Kensey | |
| 5,108,420 A | 4/1992 | Marks | |
| 5,171,252 A | 12/1992 | Friedland | |
| 5,171,259 A * | 12/1992 | Inoue | 606/213 |
| 5,192,300 A | 3/1993 | Fowler | |
| 5,192,301 A | 3/1993 | Kamiya et al. | |
| 5,192,302 A | 3/1993 | Kensey et al. | |
| 5,222,974 A | 6/1993 | Kensey et al. | |
| 5,246,441 A | 9/1993 | Ross et al. | |
| 5,279,572 A | 1/1994 | Hokama | |
| 5,282,827 A | 2/1994 | Kensey et al. | |
| 5,292,332 A * | 3/1994 | Lee | 606/213 |
| 5,306,254 A | 4/1994 | Nash et al. | |
| 5,312,435 A | 5/1994 | Nash et al. | |
| 5,334,210 A | 8/1994 | Gianturco | |
| 5,350,399 A * | 9/1994 | Erlebacher et al. | 606/213 |
| 5,350,400 A | 9/1994 | Esposito et al. | |
| 5,385,554 A | 1/1995 | Brimhall | |
| RE34,866 E | 2/1995 | Kensey et al. | |
| 5,391,183 A | 2/1995 | Janzen et al. | |
| 5,411,520 A | 5/1995 | Nash et al. | |
| 5,443,481 A | 8/1995 | Lee | |
| 5,451,235 A | 9/1995 | Lock et al. | |
| 5,474,557 A | 12/1995 | Mai | |
| 5,478,352 A | 12/1995 | Fowler | |
| 5,478,353 A | 12/1995 | Yoon | |
| 5,486,195 A | 1/1996 | Myers et al. | |
| 5,531,759 A * | 7/1996 | Kensey et al. | 606/213 |
| 5,540,716 A | 7/1996 | Hlavacek | |
| 5,545,178 A | 8/1996 | Kensey et al. | |
| 5,549,633 A | 8/1996 | Evans et al. | |
| 5,591,204 A | 1/1997 | Janzen et al. | |
| 5,593,422 A | 1/1997 | Muijs Van de Moer et al. | |
| 5,620,461 A | 4/1997 | Muijs Van de Moer et al. | |
| 5,630,833 A | 5/1997 | Katsaros et al. | |
| 5,634,936 A | 6/1997 | Linden et al. | |
| 5,643,317 A | 7/1997 | Pavcnik et al. | |
| 5,649,959 A | 7/1997 | Hannam et al. | |
| 5,662,681 A * | 9/1997 | Nash et al. | 606/213 |
| 5,674,231 A | 10/1997 | Green et al. | |
| 5,676,689 A | 10/1997 | Kensey et al. | |
| 5,690,674 A | 11/1997 | Diaz | |
| 5,700,277 A | 12/1997 | Nash et al. | |
| 5,702,421 A | 12/1997 | Schneidt | |
| 5,709,707 A | 1/1998 | Lock et al. | |
| 5,725,498 A | 3/1998 | Janzen et al. | |
| 5,728,132 A | 3/1998 | Van Tassel et al. | |
| 5,728,133 A | 3/1998 | Kontos | |
| 5,741,297 A | 4/1998 | Simon | |
| 5,782,860 A | 7/1998 | Epstein et al. | |
| 5,782,861 A | 7/1998 | Cragg et al. | |
| 5,810,846 A | 9/1998 | Virnich et al. | |
| 5,810,884 A * | 9/1998 | Kim | 606/213 |
| 5,820,628 A | 10/1998 | Middleman et al. | |
| 5,861,003 A | 1/1999 | Latson et al. | |
| 5,893,856 A * | 4/1999 | Jacob et al. | 606/151 |
| 5,910,155 A | 6/1999 | Ratcliff et al. | |
| 5,916,235 A | 6/1999 | Guglielmi | |
| 5,916,236 A | 6/1999 | Muijs Van de Moer et al. | |
| 5,919,207 A | 7/1999 | Taheri | |
| 5,964,782 A | 10/1999 | Lafontaine et al. | |
| 5,976,159 A | 11/1999 | Bolduc et al. | |
| 5,976,174 A | 11/1999 | Ruiz | |
| 5,984,949 A | 11/1999 | Levin | |
| 6,001,110 A | 12/1999 | Adams | |
| 6,007,563 A | 12/1999 | Nash et al. | |
| 6,010,517 A | 1/2000 | Baccaro | |
| 6,015,417 A | 1/2000 | Reynolds, Jr. | |
| 6,033,427 A | 3/2000 | Lee | |
| 6,048,357 A | 4/2000 | Kontos | |
| 6,048,358 A | 4/2000 | Barak | |
| 6,056,768 A | 5/2000 | Cates et al. | |
| 6,063,085 A | 5/2000 | Tay et al. | |
| 6,071,300 A | 6/2000 | Brenneman et al. | |
| 6,077,281 A | 6/2000 | Das | |
| 6,080,182 A | 6/2000 | Shaw et al. | |
| 6,080,183 A * | 6/2000 | Tsugita et al. | 606/213 |
| 6,113,611 A | 9/2000 | Allen et al. | |
| 6,117,159 A | 9/2000 | Huebsch et al. | |
| 6,120,524 A | 9/2000 | Taheri | |
| 6,126,675 A * | 10/2000 | Shchervinsky et al. | 606/213 |
| 6,139,564 A | 10/2000 | Teoh | |
| 6,171,320 B1 | 1/2001 | Monassevitch | |
| 6,171,329 B1 | 1/2001 | Shaw et al. | |
| 6,174,322 B1 | 1/2001 | Schneidt | |
| 6,179,863 B1 | 1/2001 | Kensey et al. | |
| 6,197,042 B1 | 3/2001 | Ginn et al. | |
| 6,206,907 B1 | 3/2001 | Marino et al. | |
| 6,228,096 B1 | 5/2001 | Marchand | |
| 6,231,561 B1 | 5/2001 | Frazier et al. | |
| 6,251,122 B1 | 6/2001 | Tsukernik | |
| 6,261,309 B1 | 7/2001 | Urbanski | |
| 6,270,515 B1 | 8/2001 | Linden et al. | |
| 6,277,140 B2 | 8/2001 | Ginn et al. | |
| 6,328,727 B1 | 12/2001 | Frazier et al. | |
| 6,334,865 B1 | 1/2002 | Redmond et al. | |
| 6,336,914 B1 | 1/2002 | Gillespie, III | |
| 6,342,064 B1 | 1/2002 | Koike et al. | |
| 6,346,117 B1 | 2/2002 | Greenhalgh | |
| 6,350,270 B1 | 2/2002 | Roue | |
| 6,350,274 B1 | 2/2002 | Li | |
| 6,355,052 B1 | 3/2002 | Neuss et al. | |
| 6,368,341 B1 | 4/2002 | Abrahamson | |
| 6,391,037 B1 | 5/2002 | Greenhalgh | |
| 6,391,048 B1 | 5/2002 | Ginn et al. | |
| 6,409,739 B1 | 6/2002 | Nobles et al. | |
| 6,419,669 B1 | 7/2002 | Frazier et al. | |
| 6,425,911 B1 | 7/2002 | Akerfeldt et al. | |
| 6,436,088 B2 | 8/2002 | Frazier et al. | |
| 6,447,524 B1 | 9/2002 | Knodel et al. | |
| 6,482,179 B1 | 11/2002 | Chu et al. | |
| 6,508,828 B1 | 1/2003 | Akerfeldt et al. | |
| 6,537,299 B1 | 3/2003 | Hogendijk et al. | |
| 6,569,185 B2 | 5/2003 | Ungs | |
| 6,585,748 B1 | 7/2003 | Jeffree | |
| 6,596,012 B2 | 7/2003 | Akerfeldt et al. | |
| 6,626,937 B1 | 9/2003 | Cox | |
| 6,682,489 B2 | 1/2004 | Tenerz et al. | |
| 6,712,836 B1 * | 3/2004 | Berg et al. | 606/213 |
| 6,712,837 B2 | 3/2004 | Akerfeldt et al. | |
| 6,749,621 B2 | 6/2004 | Pantages et al. | |
| 6,766,186 B1 | 7/2004 | Hoyns et al. | |
| 6,790,220 B2 | 9/2004 | Morris | |
| 6,846,316 B2 | 1/2005 | Abrams | |
| 6,855,153 B2 | 2/2005 | Saadat | |
| 6,960,224 B2 | 11/2005 | Marino et al. | |
| 7,025,776 B1 | 4/2006 | Houser et al. | |
| 7,033,393 B2 | 4/2006 | Gainor et al. | |
| 7,153,323 B1 | 12/2006 | Teoh et al. | |
| 7,618,438 B2 | 11/2009 | White et al. | |
| 2002/0082622 A1 | 6/2002 | Kane | |
| 2002/0165572 A1 | 11/2002 | Saadat | |
| 2003/0055451 A1 | 3/2003 | Jones et al. | |
| 2003/0088269 A1 | 5/2003 | Ashby | |
| 2003/0105487 A1 | 6/2003 | Benz et al. | |
| 2003/0187473 A1 | 10/2003 | Berenstein et al. | |
| 2004/0002764 A1 | 1/2004 | Gainor et al. | |
| 2004/0143294 A1 | 7/2004 | Corcoran et al. | |
| 2004/0153103 A1 | 8/2004 | Schwartz et al. | |
| 2004/0158287 A1 | 8/2004 | Cragg et al. | |
| 2005/0065547 A1 | 3/2005 | Marino et al. | |
| 2005/0070957 A1 | 3/2005 | Das | |
| 2005/0090859 A1 | 4/2005 | Ravlkumar | |
| 2005/0107807 A1 | 5/2005 | Nakao | |
| 2005/0192627 A1 | 9/2005 | Whisenant et al. | |
| 2005/0267524 A1 | 12/2005 | Chanduszko | |

| | | | | | |
|---|---|---|---|---|---|
| 2006/0106418 | A1 | 5/2006 | Seibold et al. | | |
| 2006/0173492 | A1 | 8/2006 | Akerfeldt et al. | | |
| 2007/0149998 | A1 | 6/2007 | Wicks et al. | | |

FOREIGN PATENT DOCUMENTS

| | | |
|---|---|---|
| EP | 0637431 | 2/1995 |
| EP | 0920842 | 6/1999 |
| WO | 9520916 | 8/1995 |
| WO | 9707741 | 3/1997 |
| WO | 9827868 | 7/1998 |
| WO | 9900055 | 1/1999 |
| WO | 9905977 | 2/1999 |
| WO | 9938454 | 8/1999 |
| WO | 2004 012601 | 2/2004 |

* cited by examiner

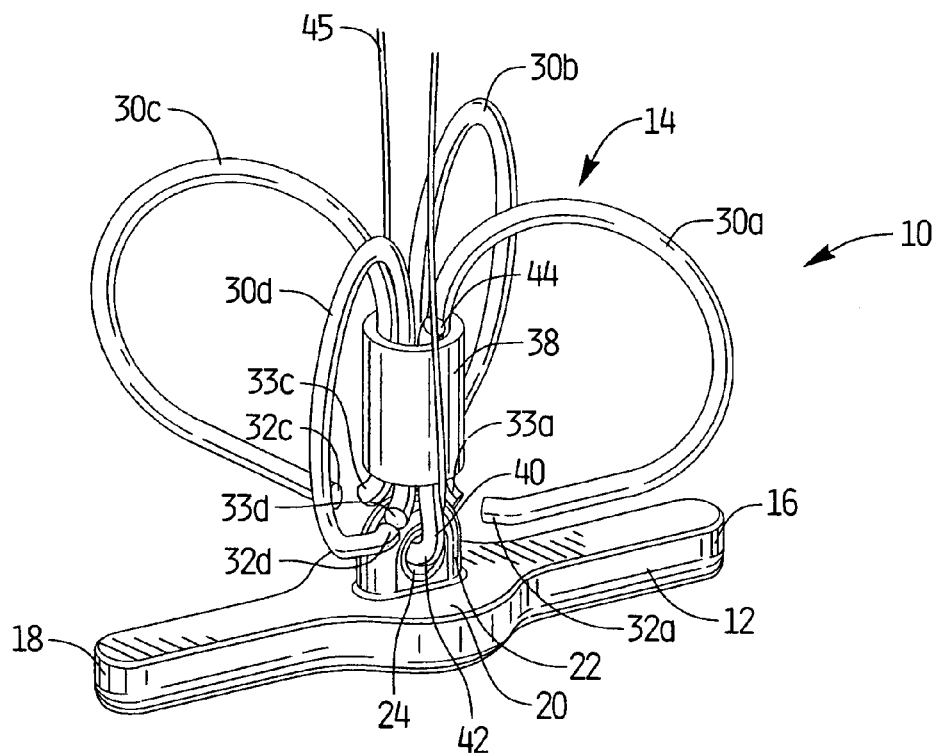
FIG_1
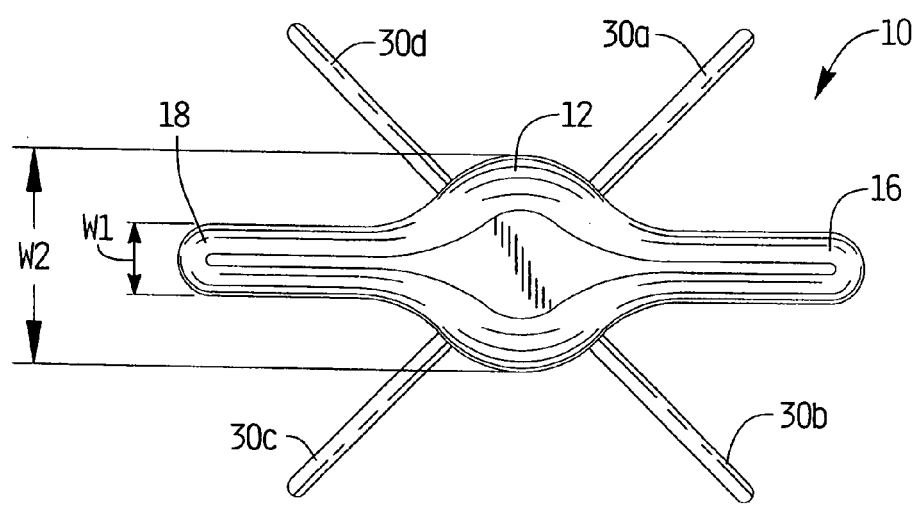
FIG_2

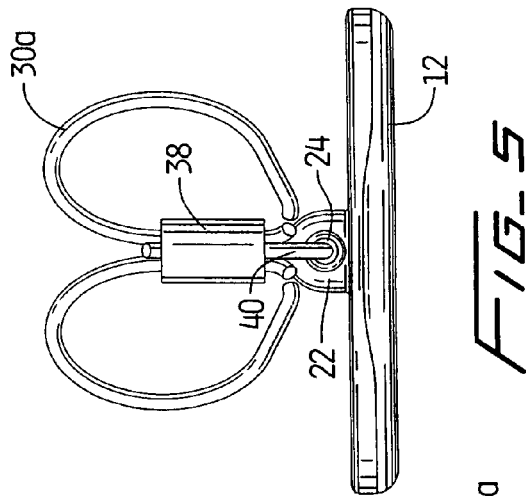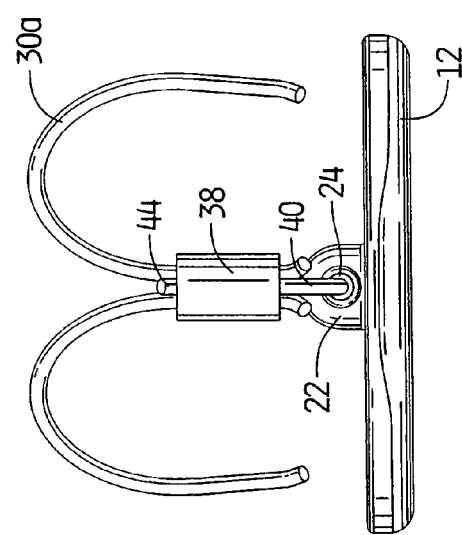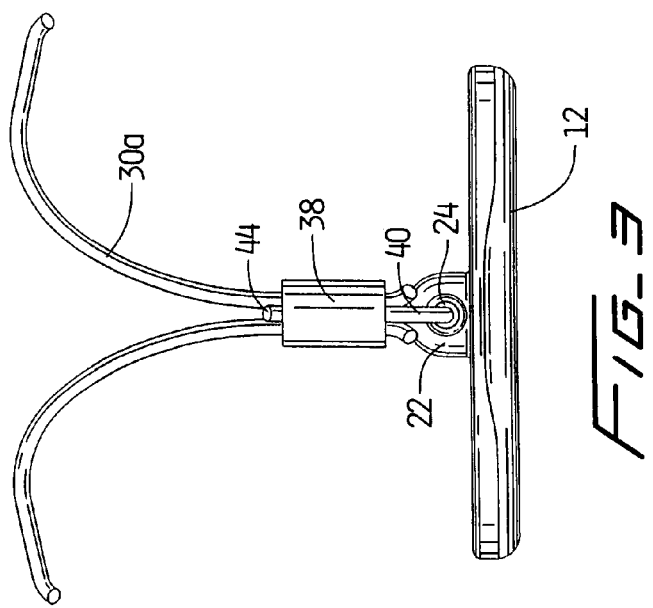

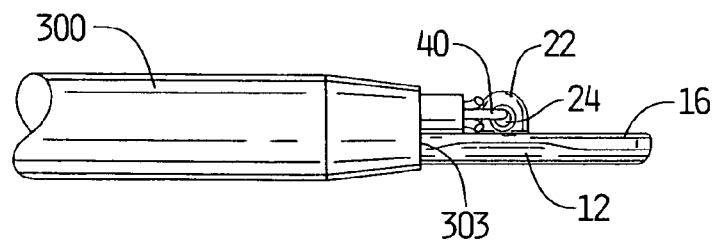
FIG_6
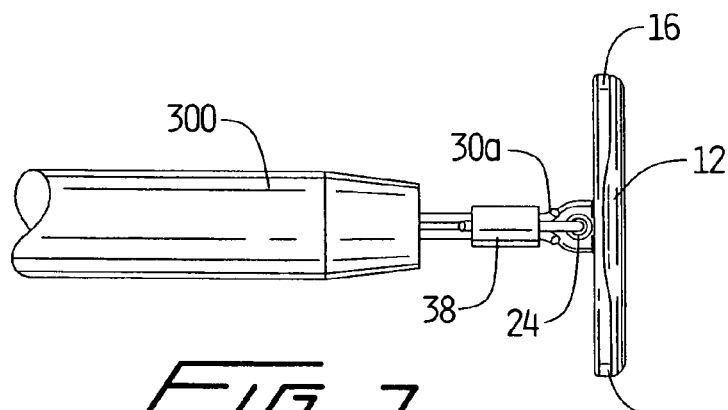
FIG_7
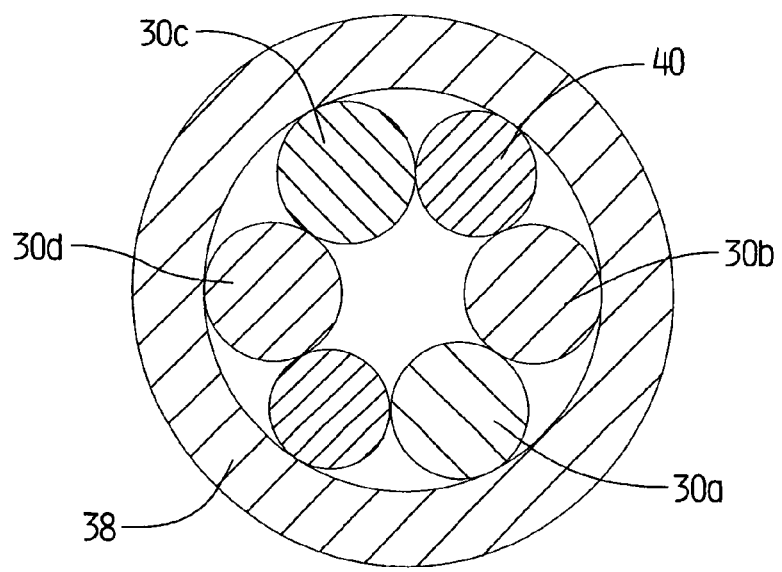
FIG_8

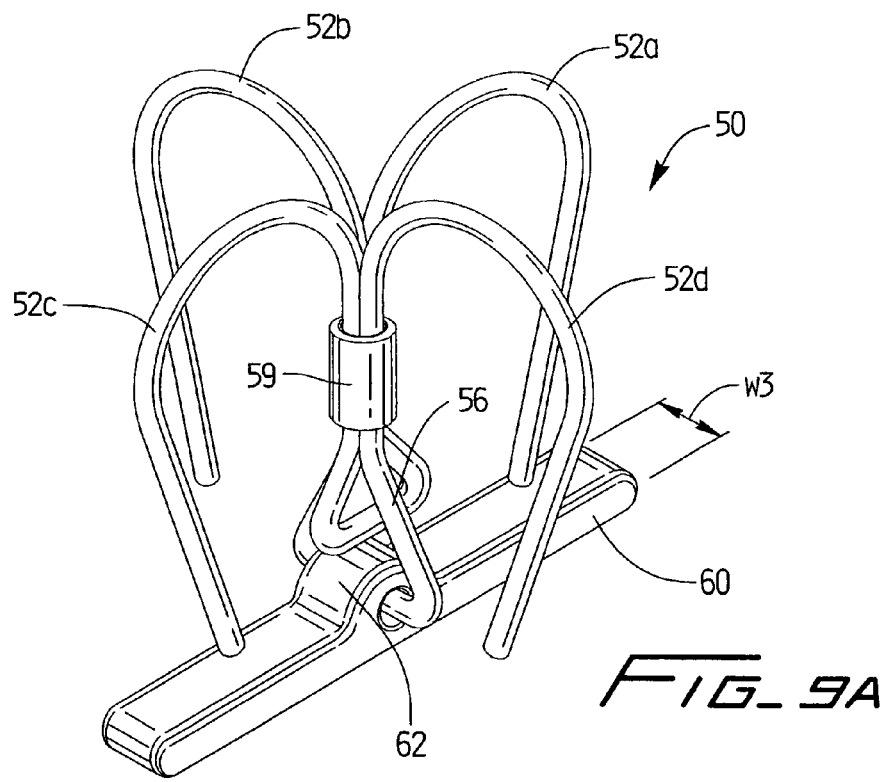
FIG_9A
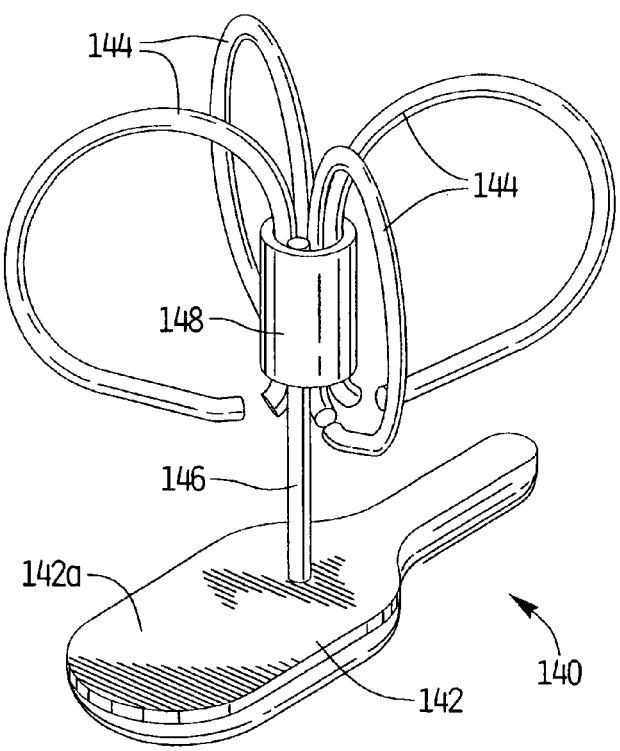
FIG_9B

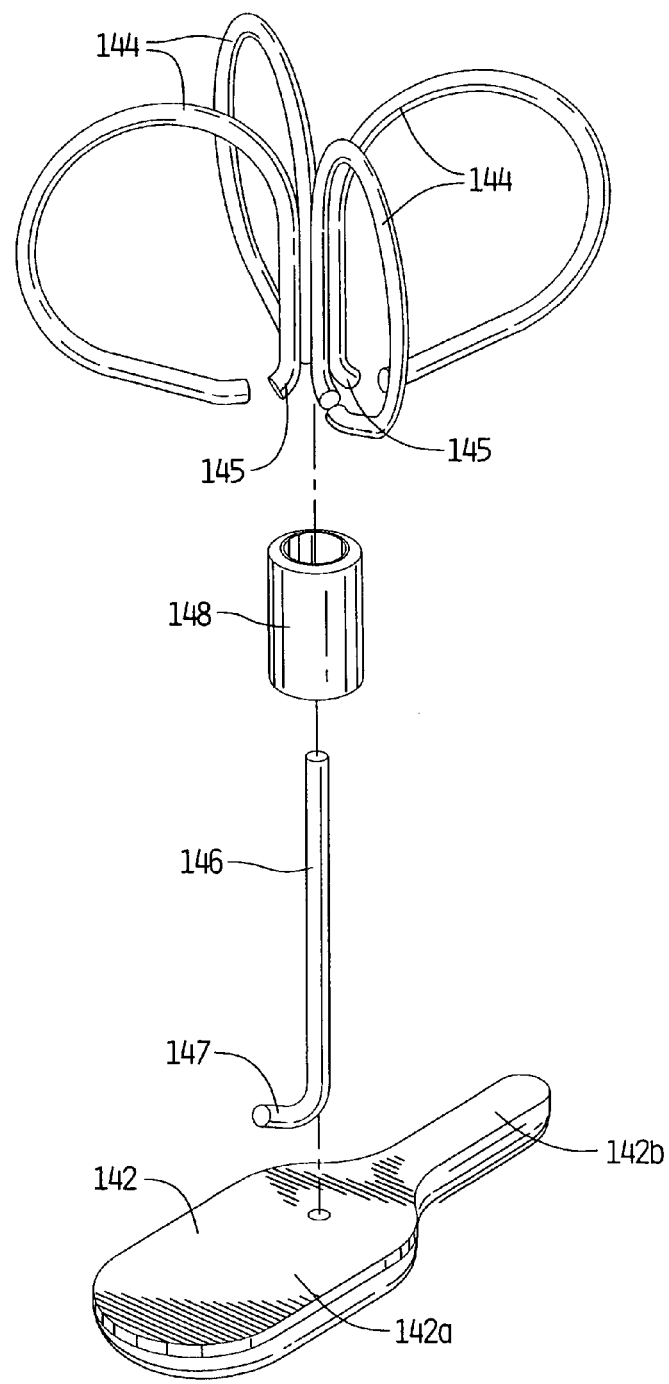
FIG_9C

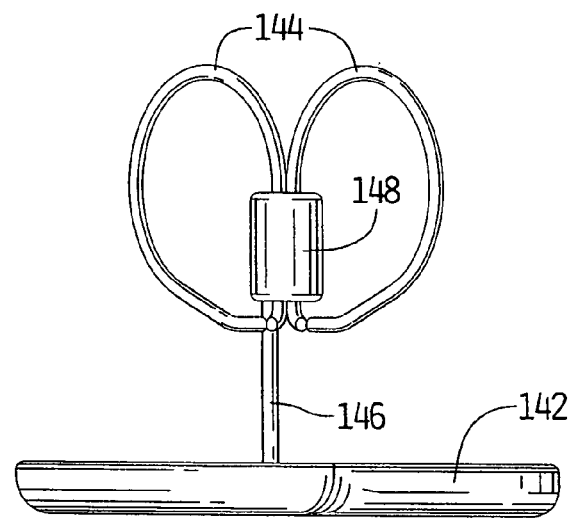
FIG_9D
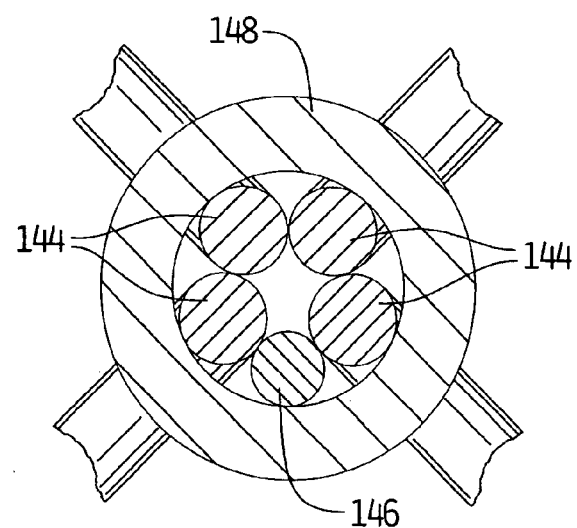
FIG_9E

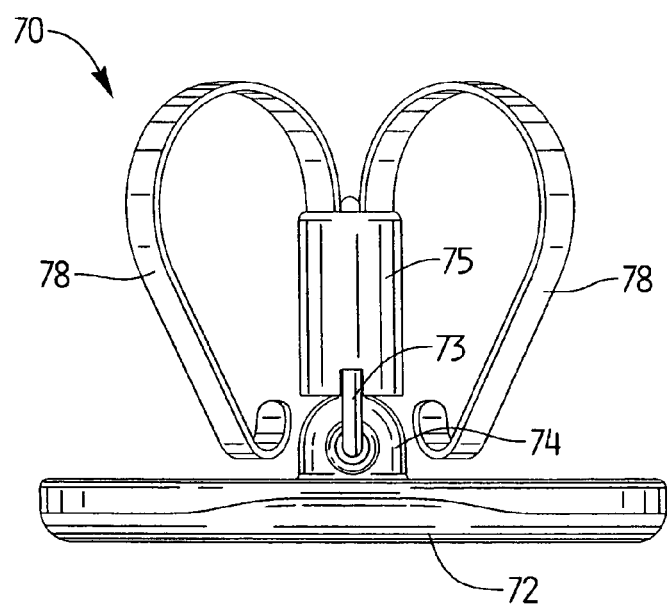
FIG_10A
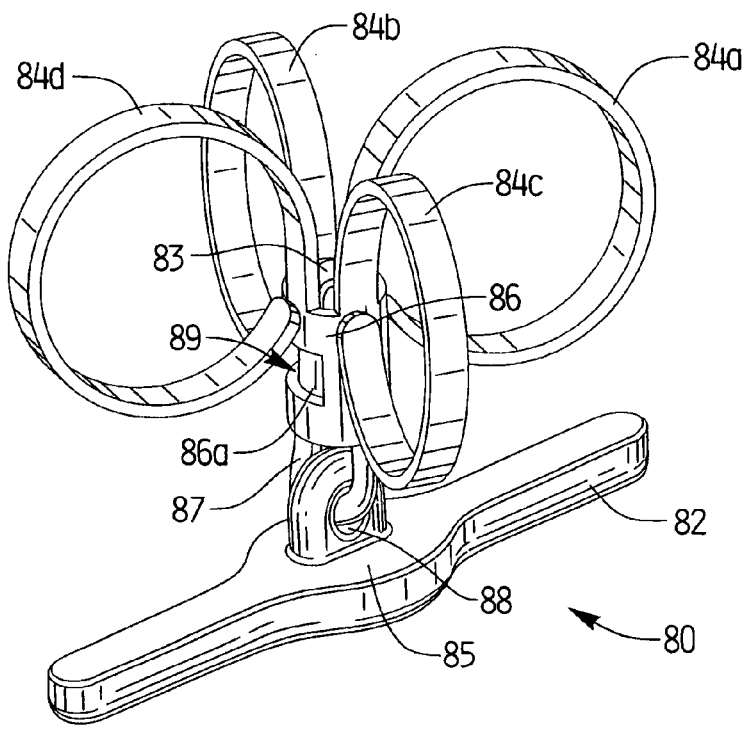
FIG_10B

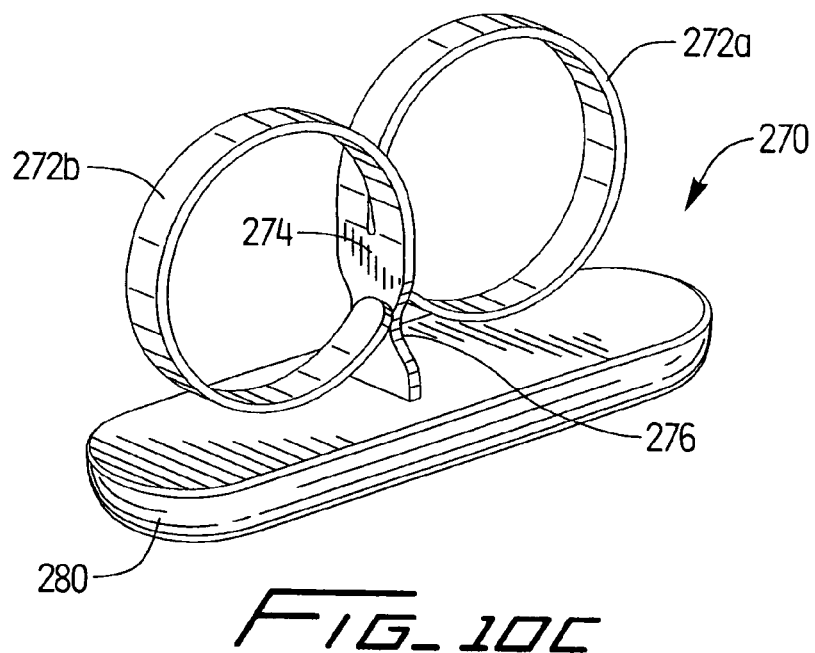
FIG_10C
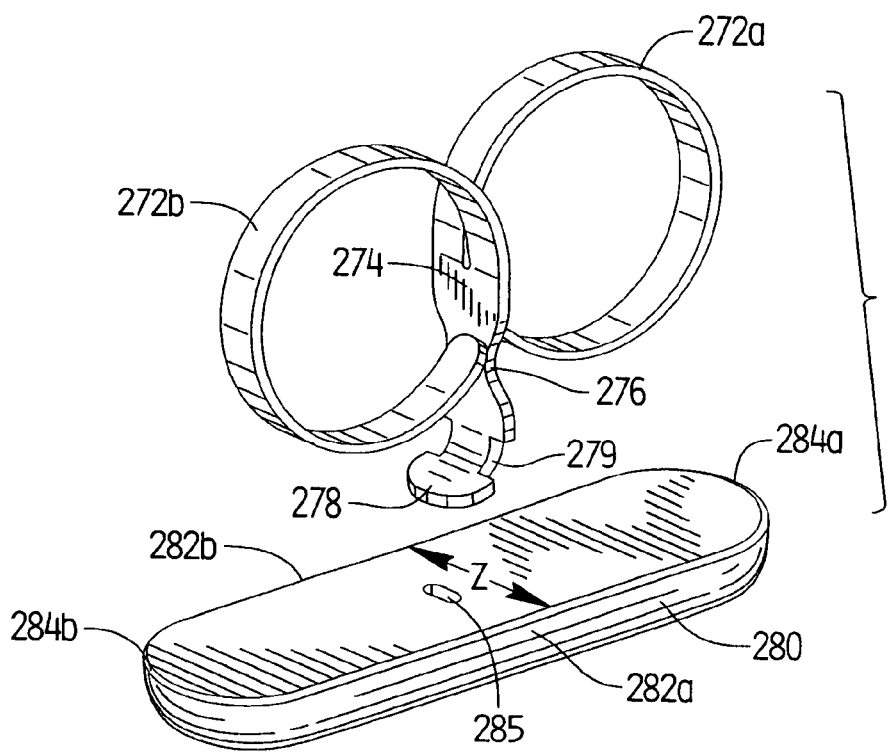
FIG_10D

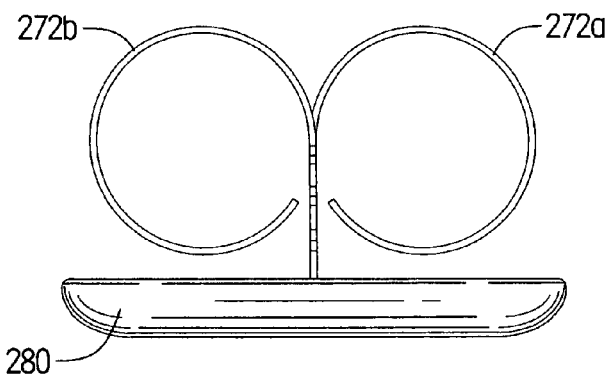
FIG_10E
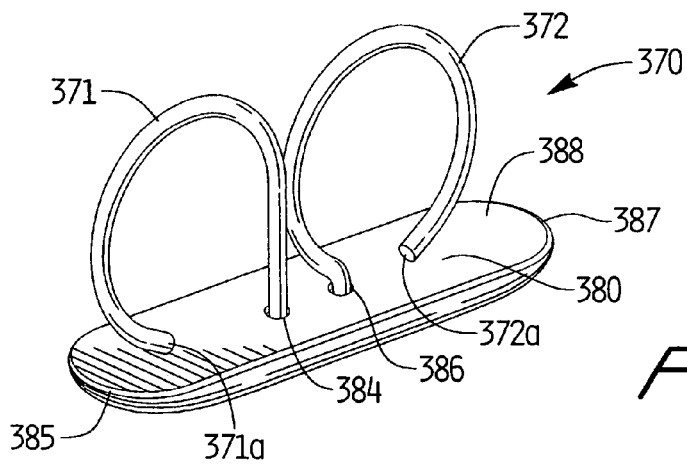
FIG_10F
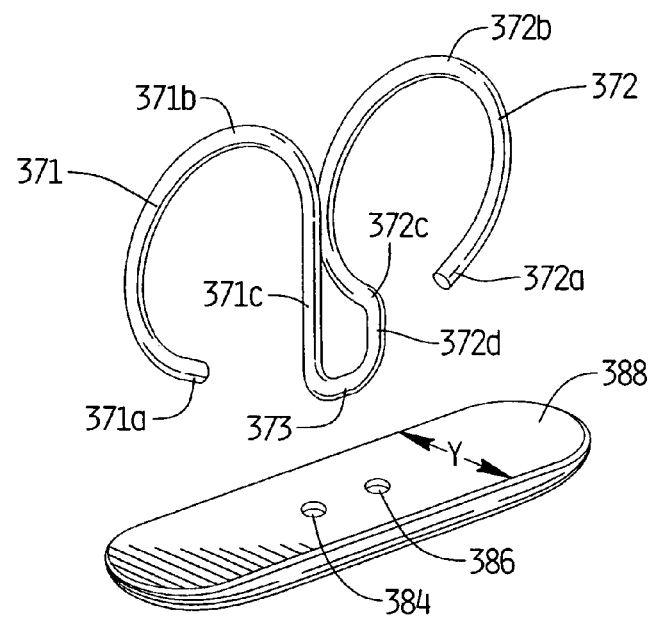
FIG_10G

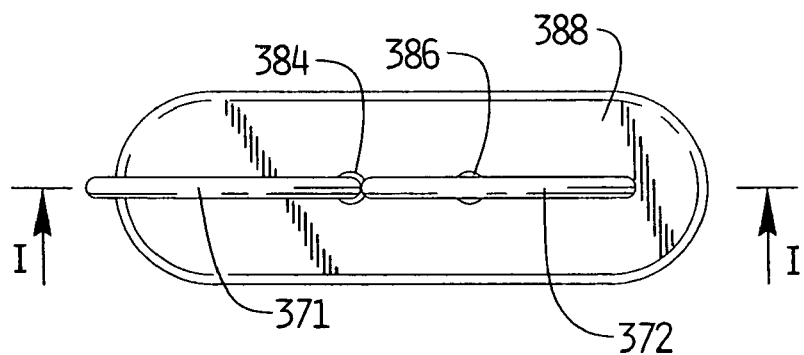
FIG_10H
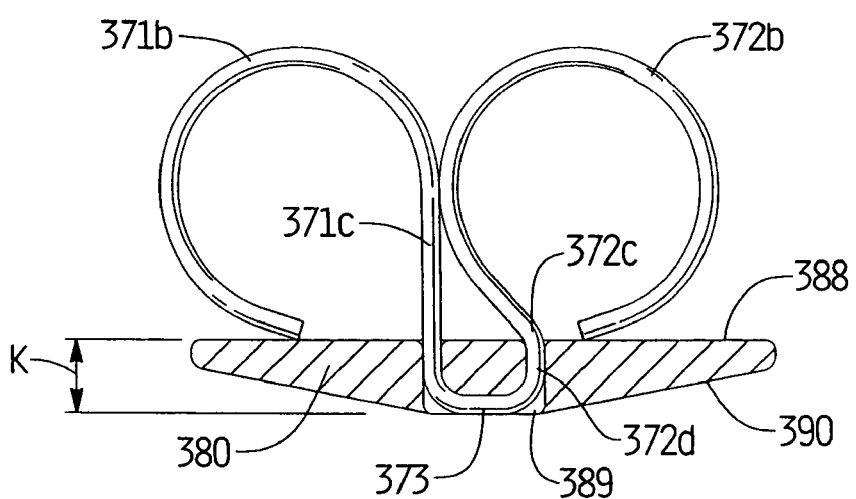
FIG_10I

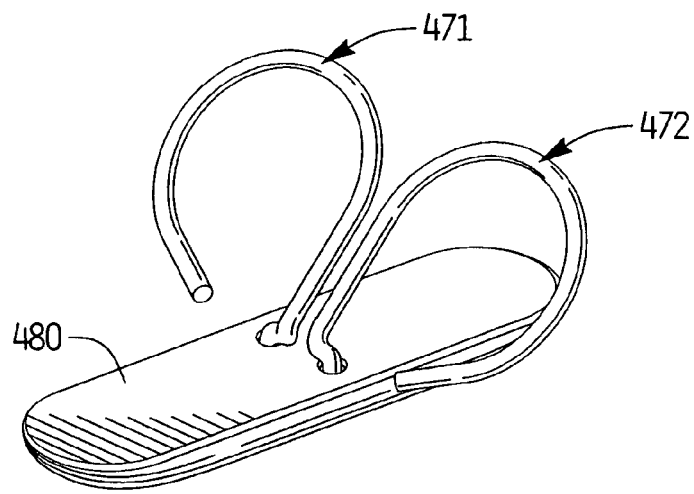
FIG_10J
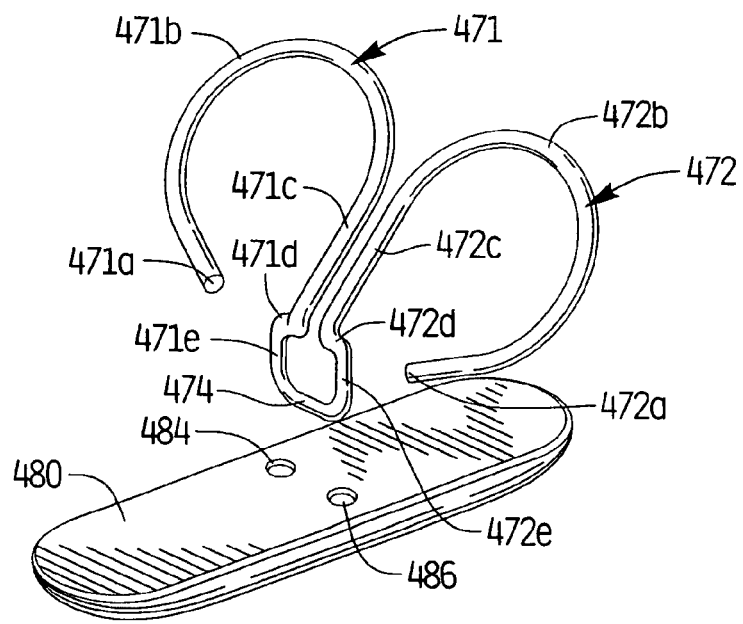
FIG_10K

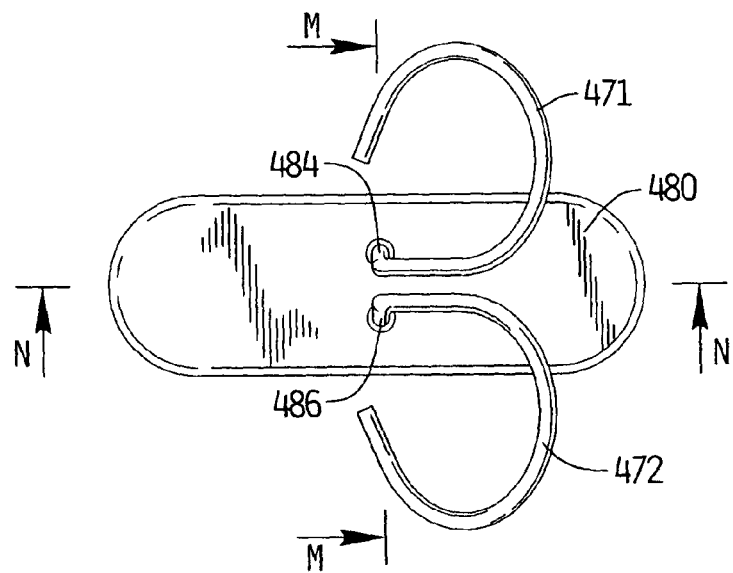
FIG_10L
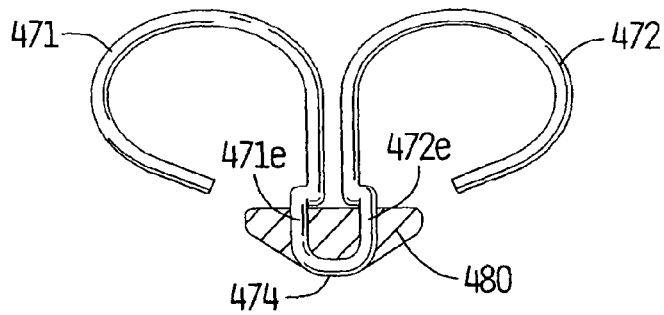
FIG_10M
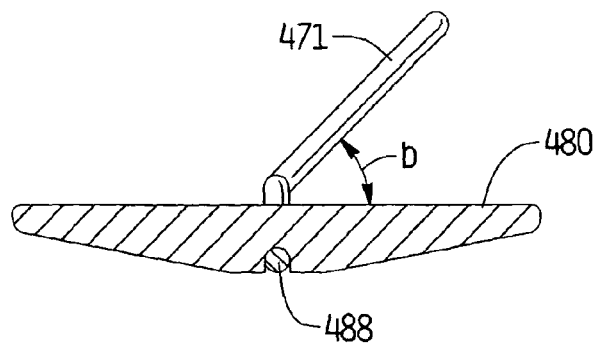
FIG_10N

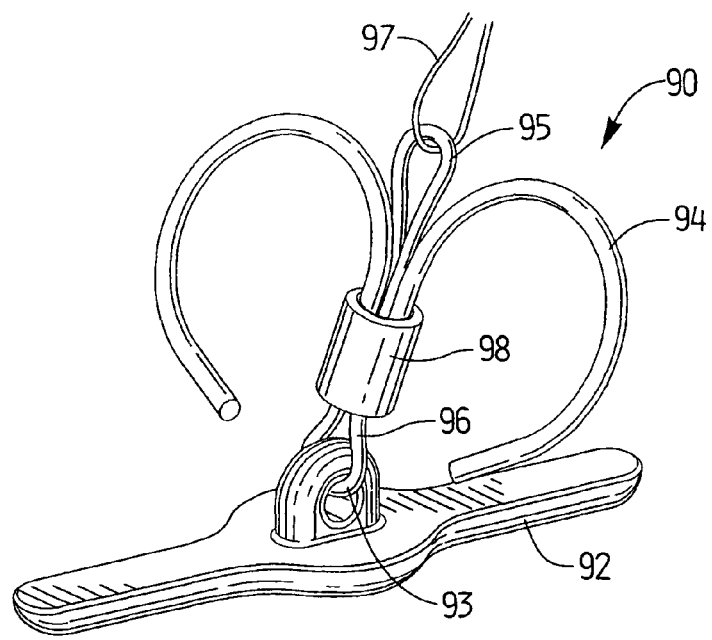
FIG_11A
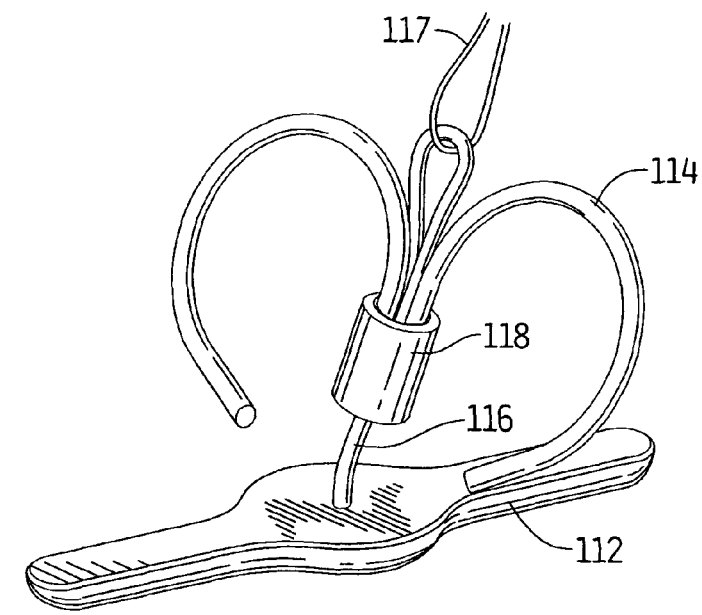
FIG_11B

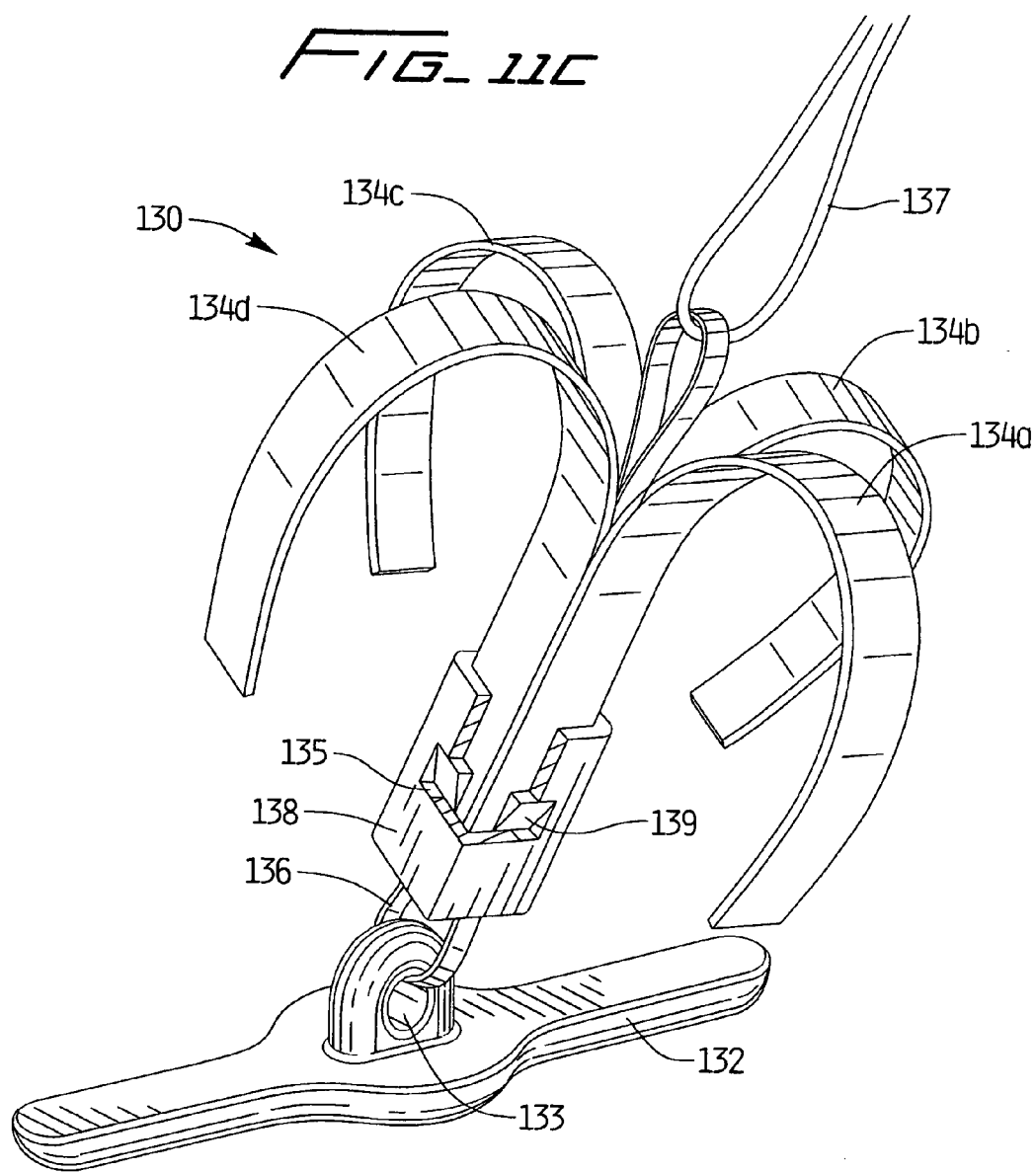
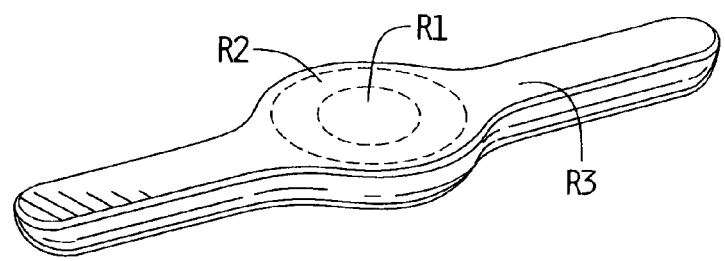

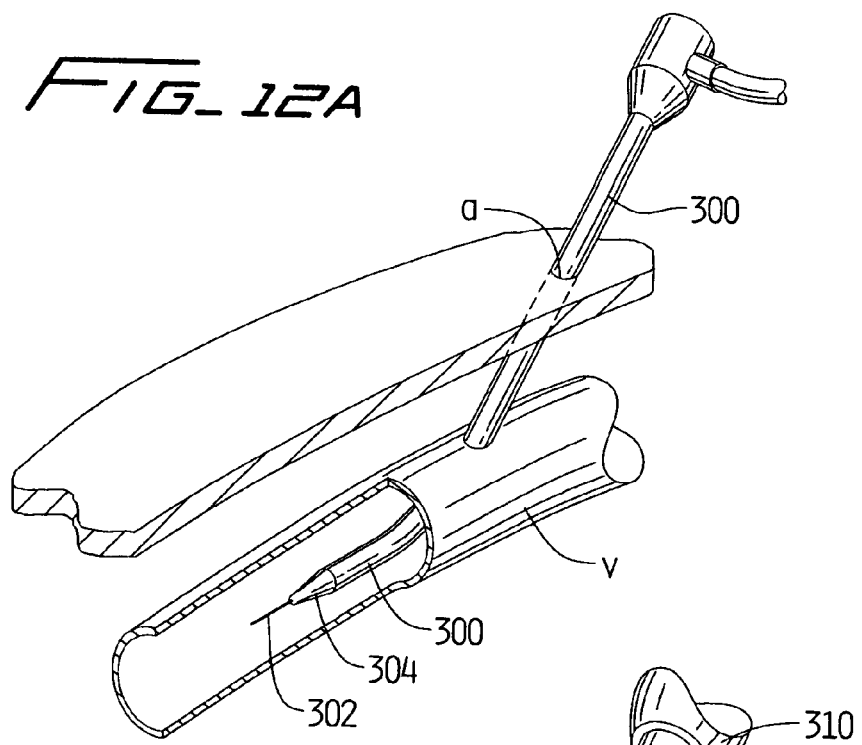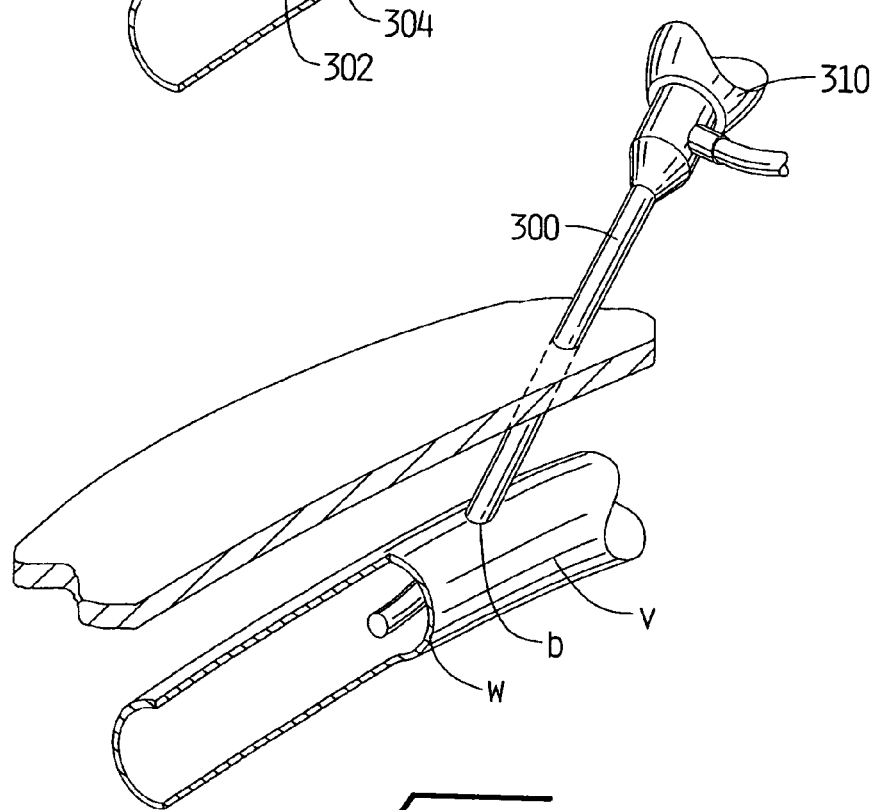

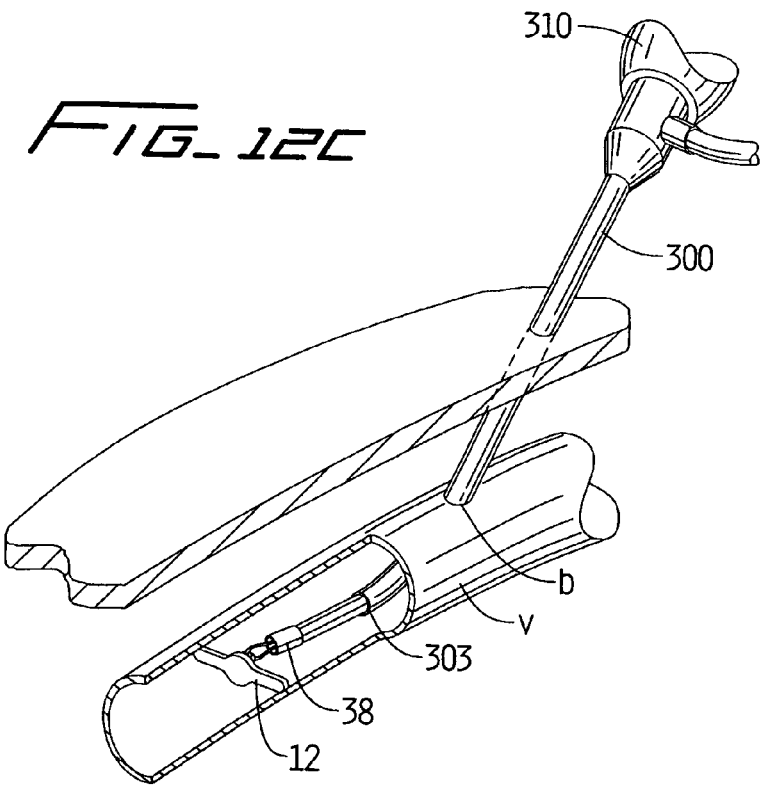
FIG_12C
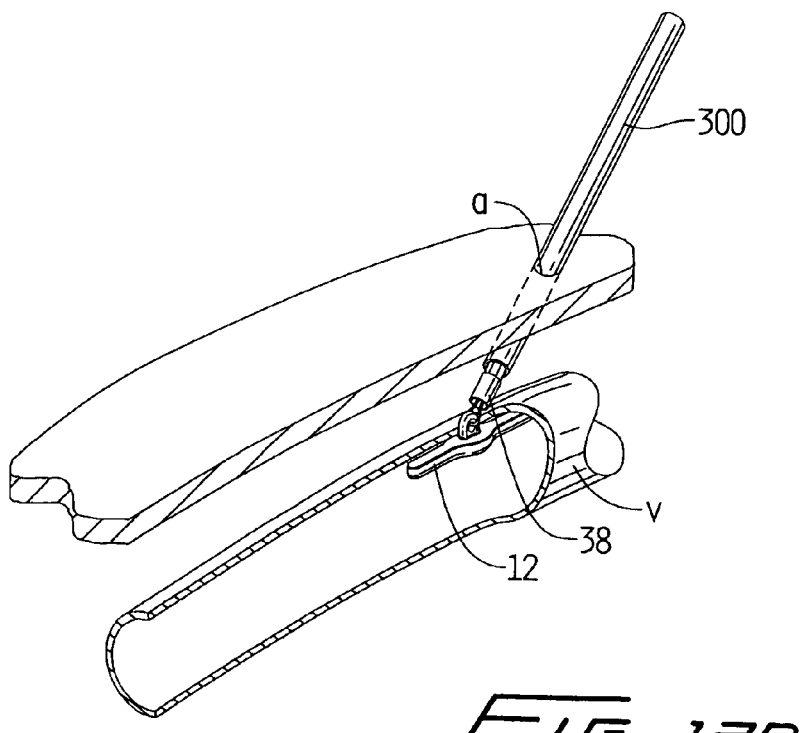
FIG_12D

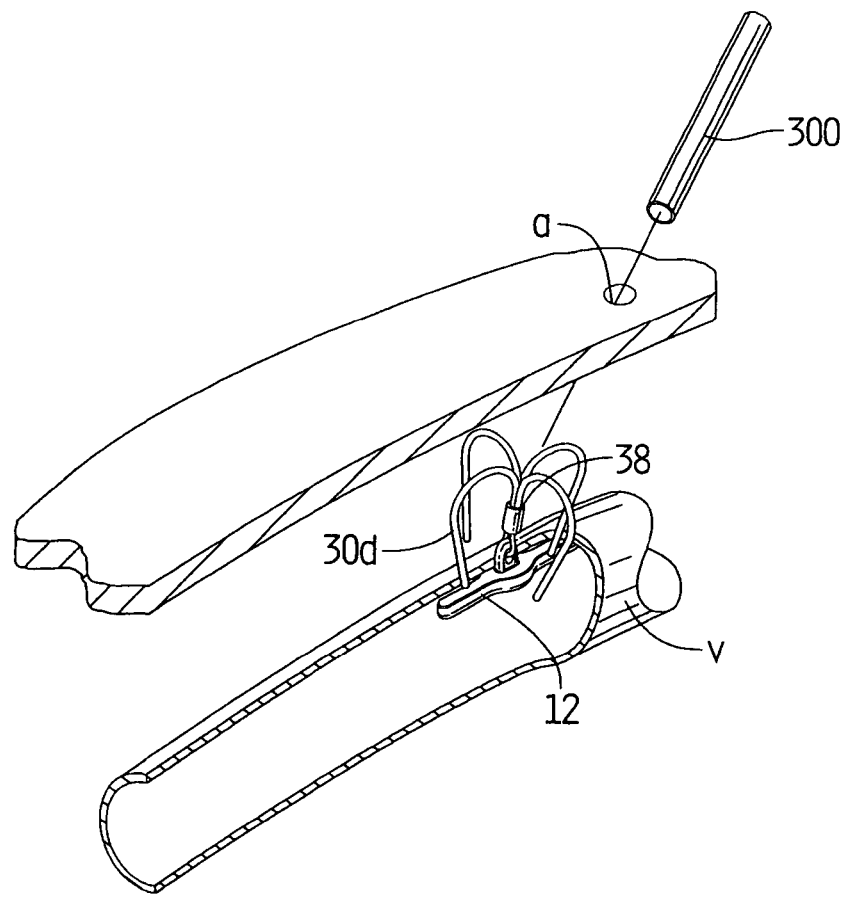
FIG_12E
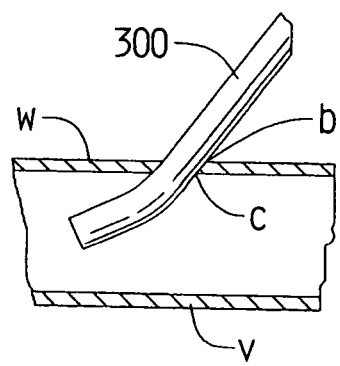
FIG_12F

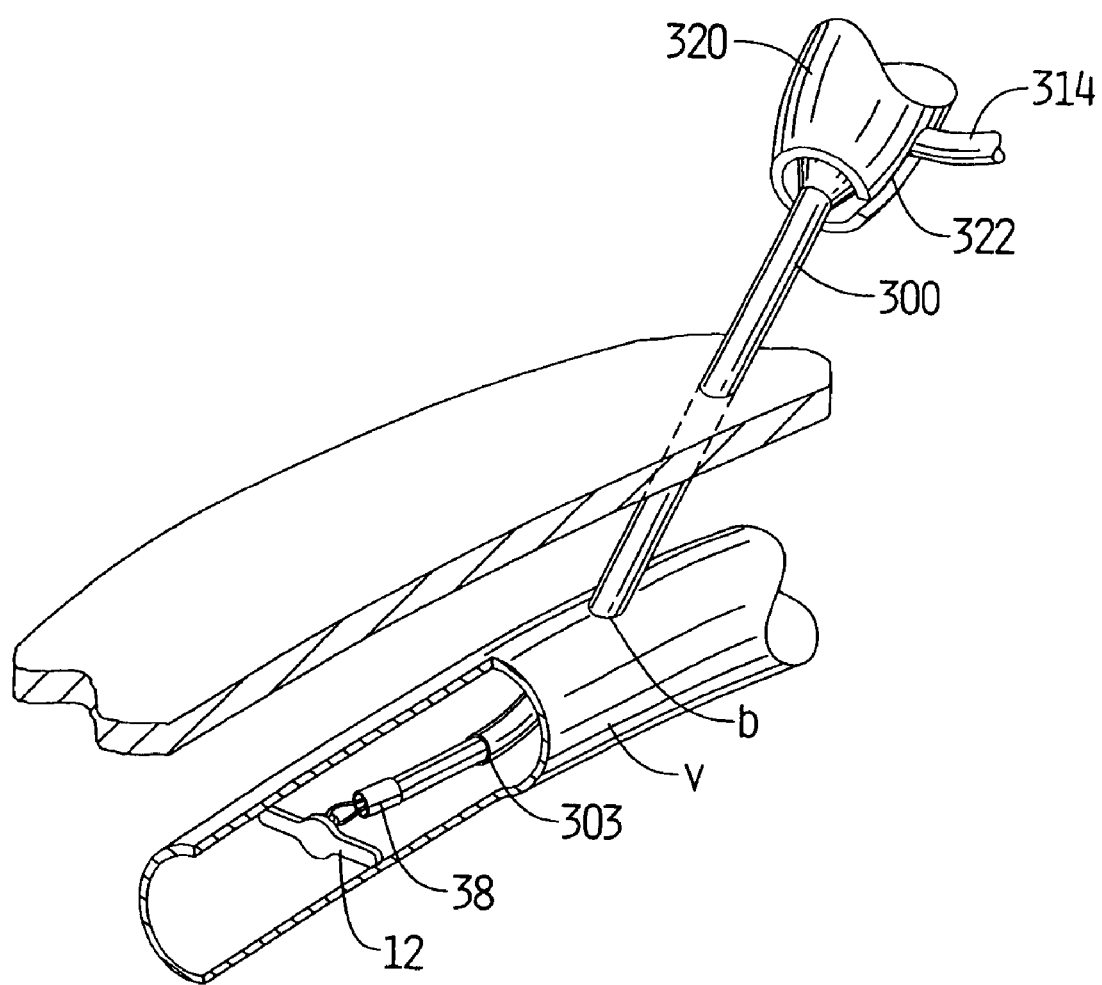

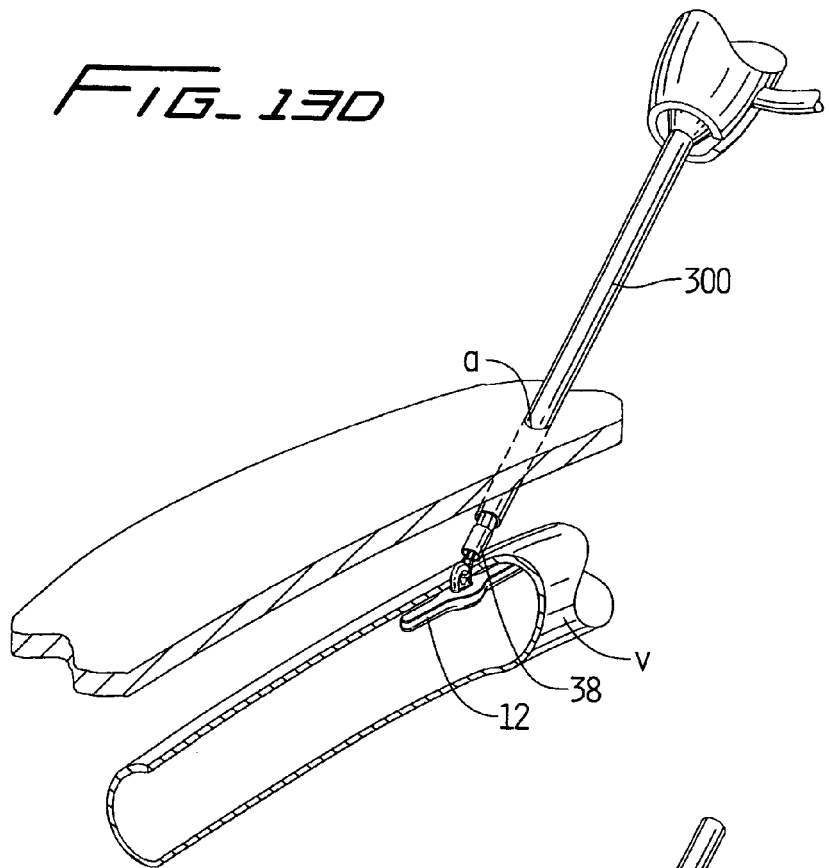
FIG_13D
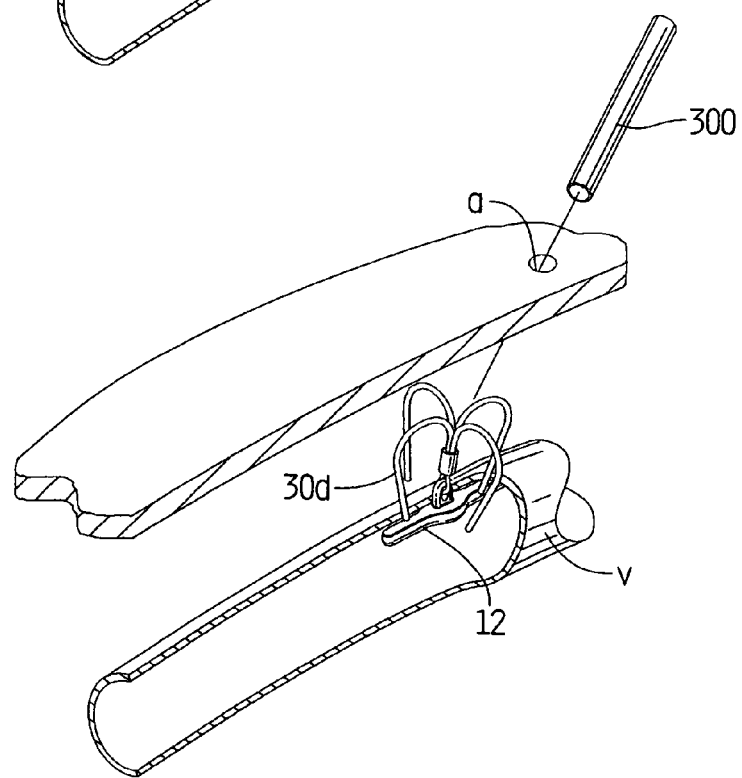
FIG_13E

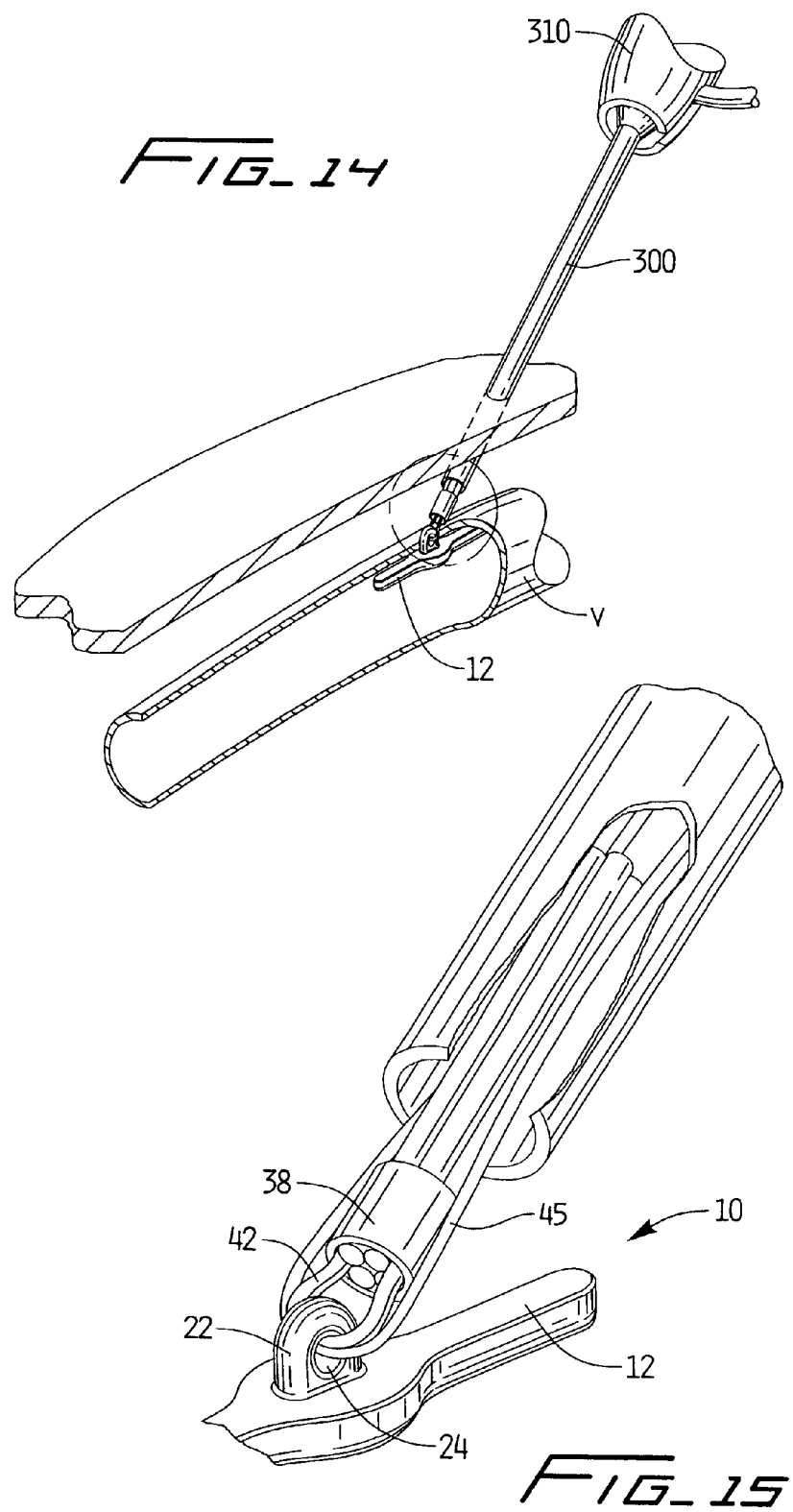

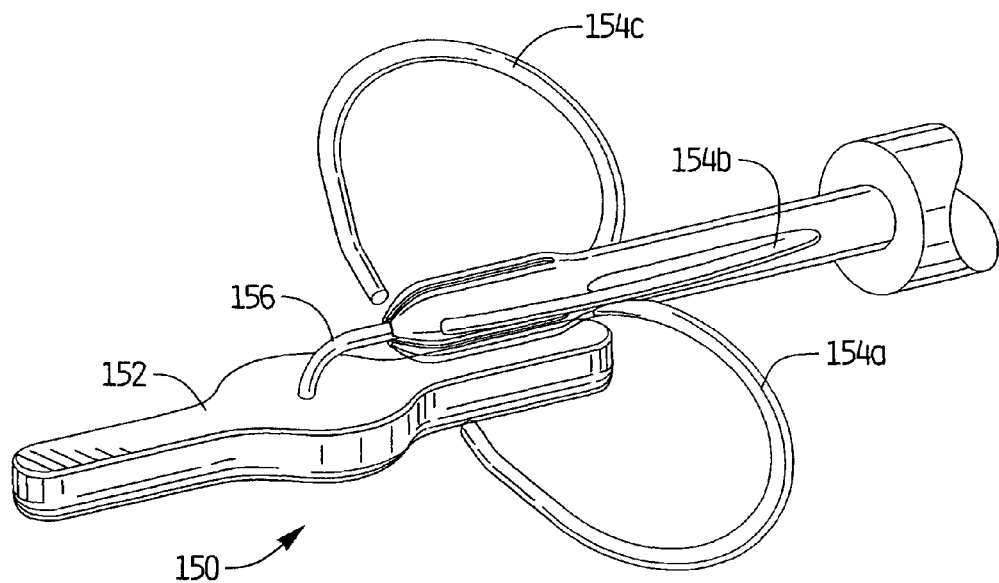
FIG_16A
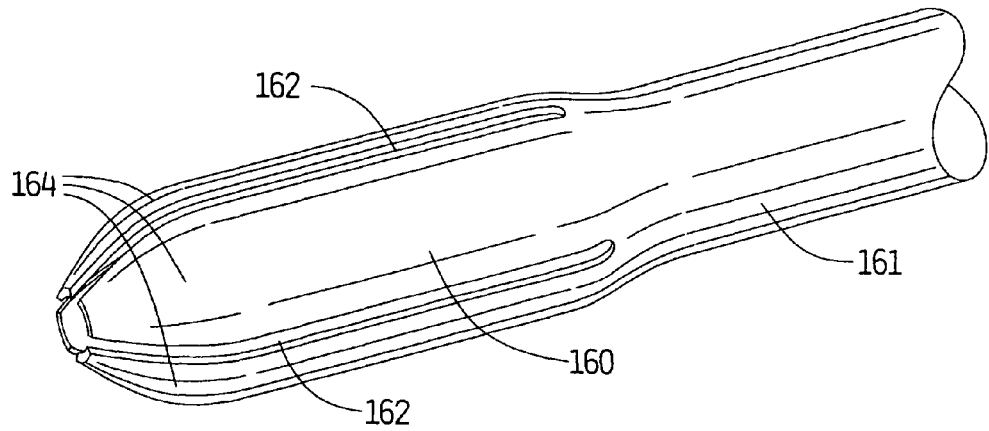
FIG_16B

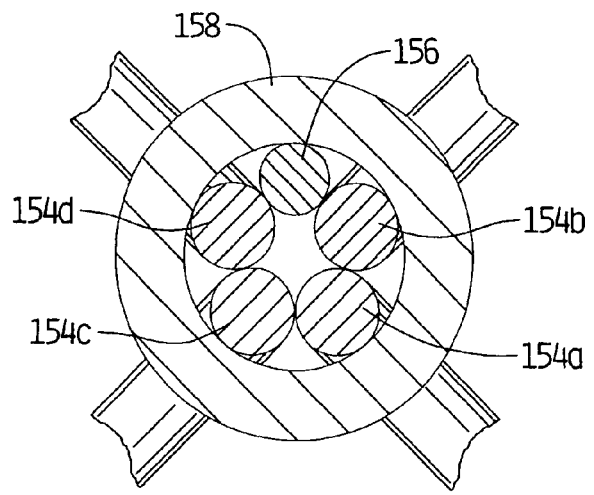
FIG_16C
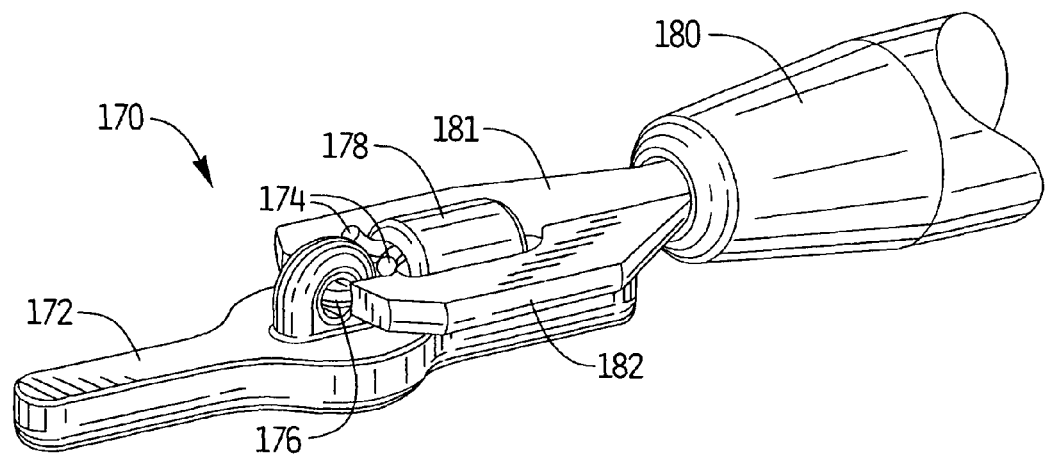
FIG_16D

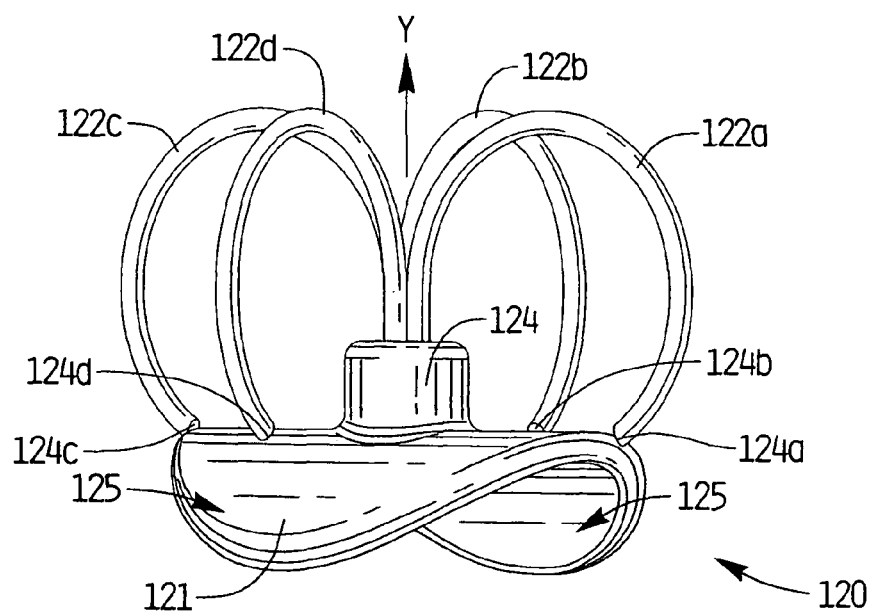
FIG_17A
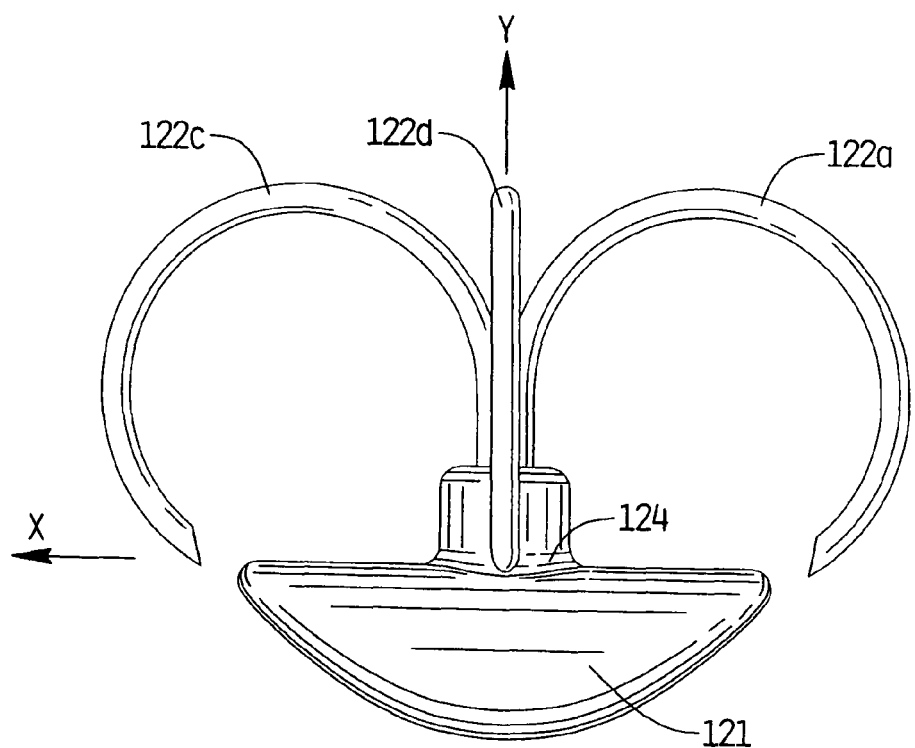
FIG_17B

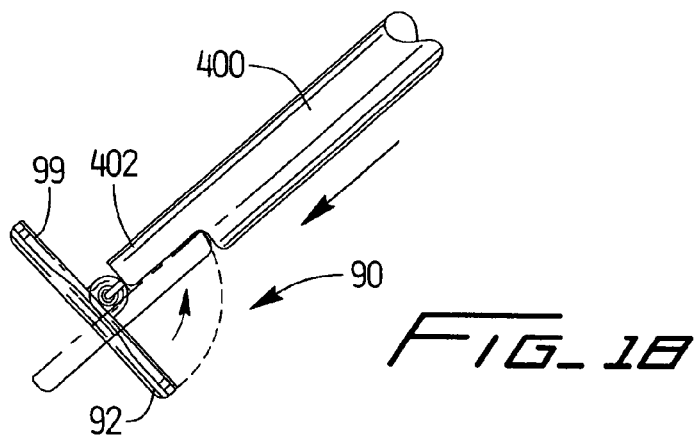
FIG_18
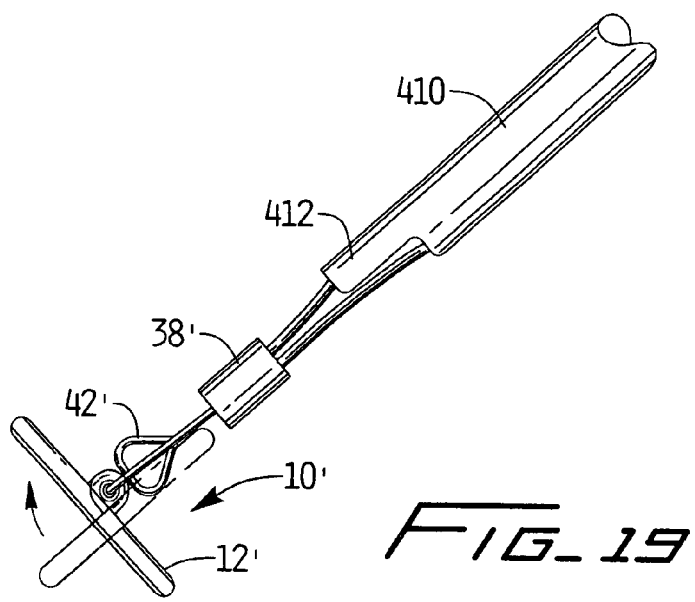
FIG_19
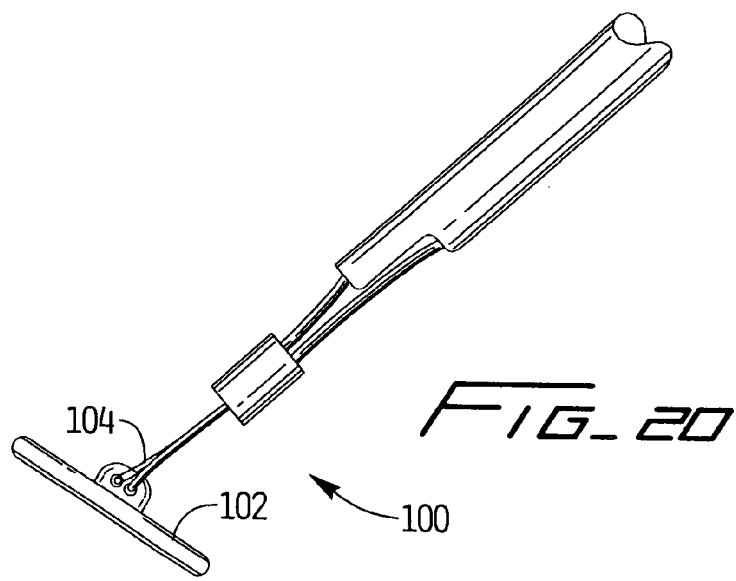
FIG_20

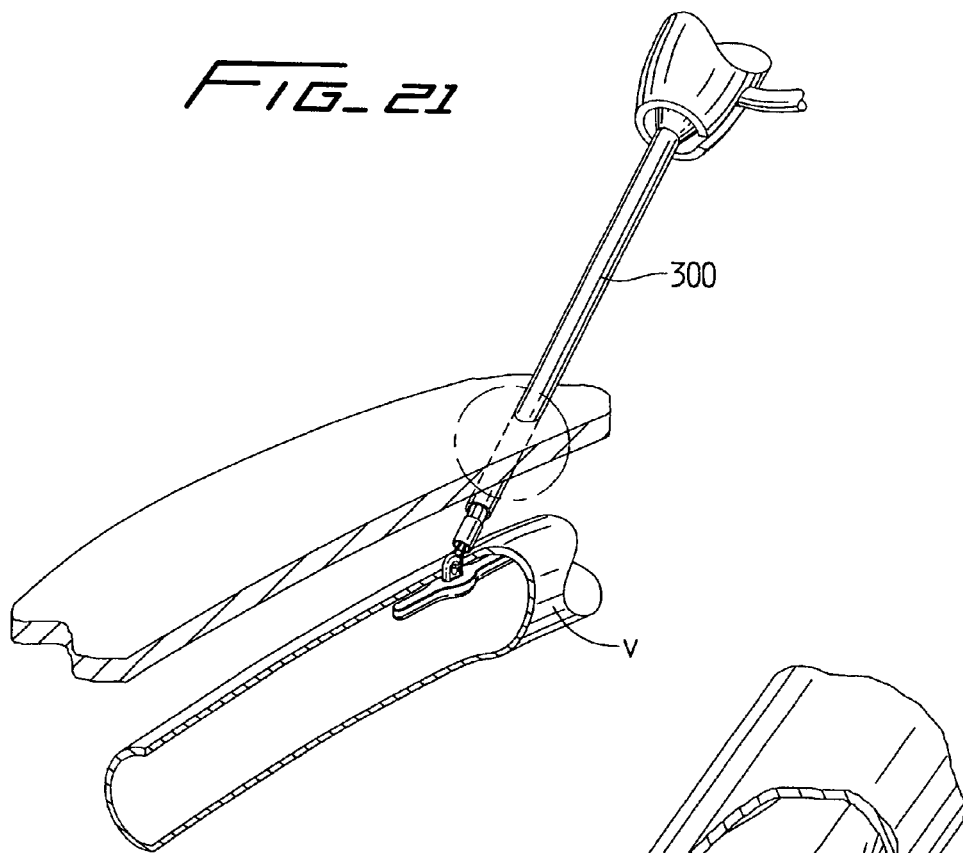
FIG_21
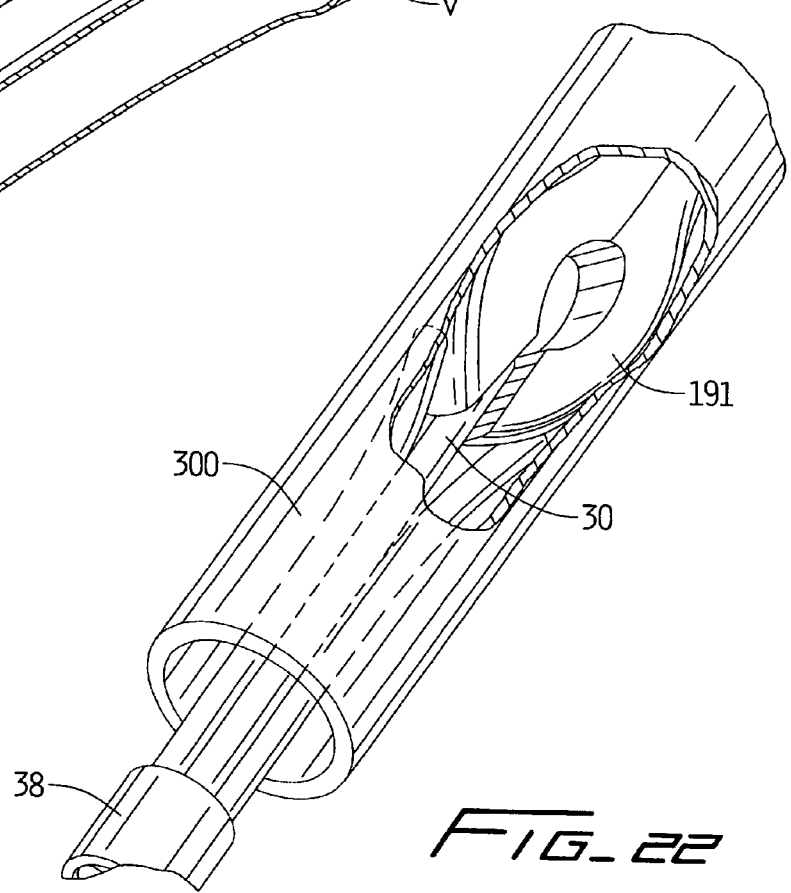
FIG_22

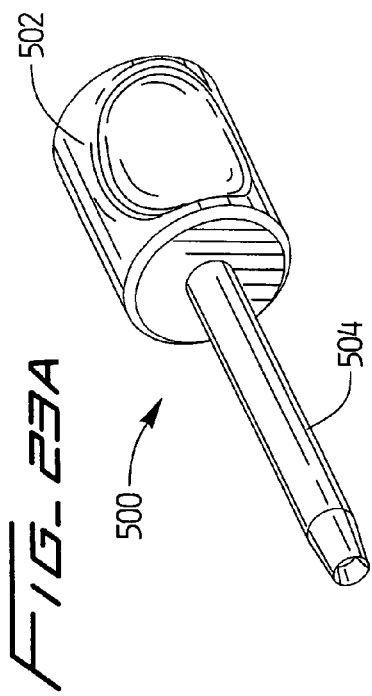
FIG._23A
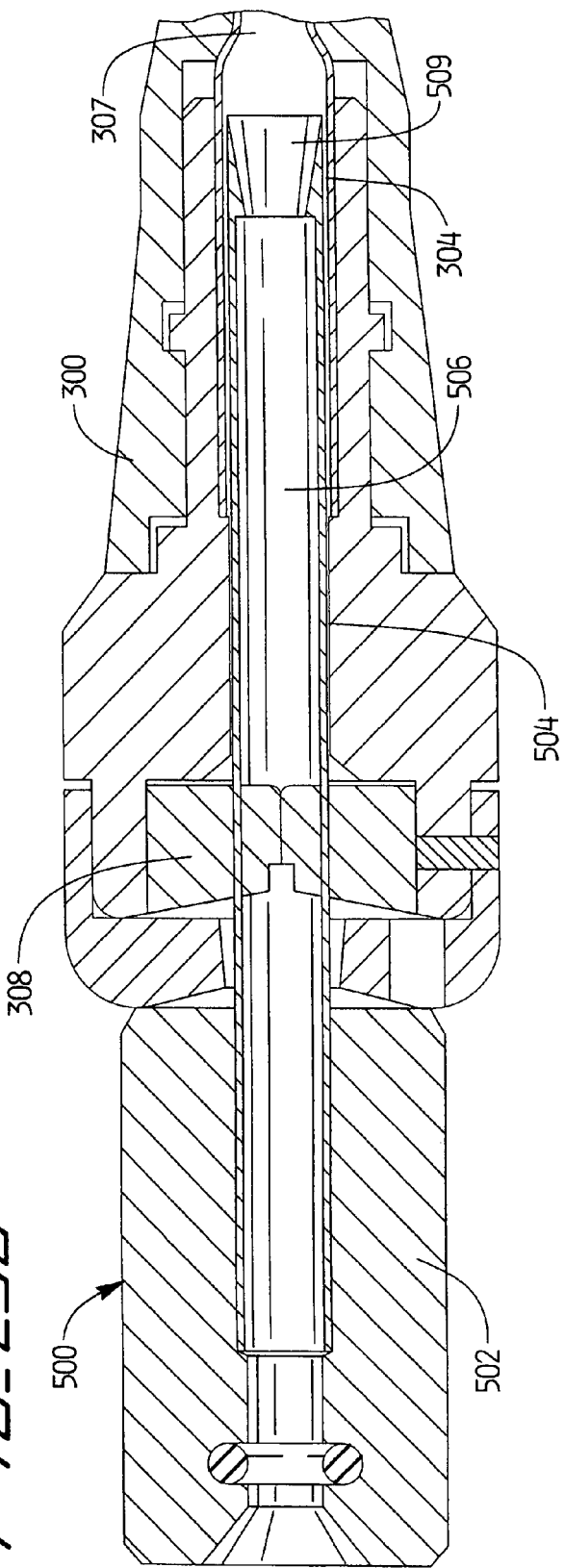
FIG._23B

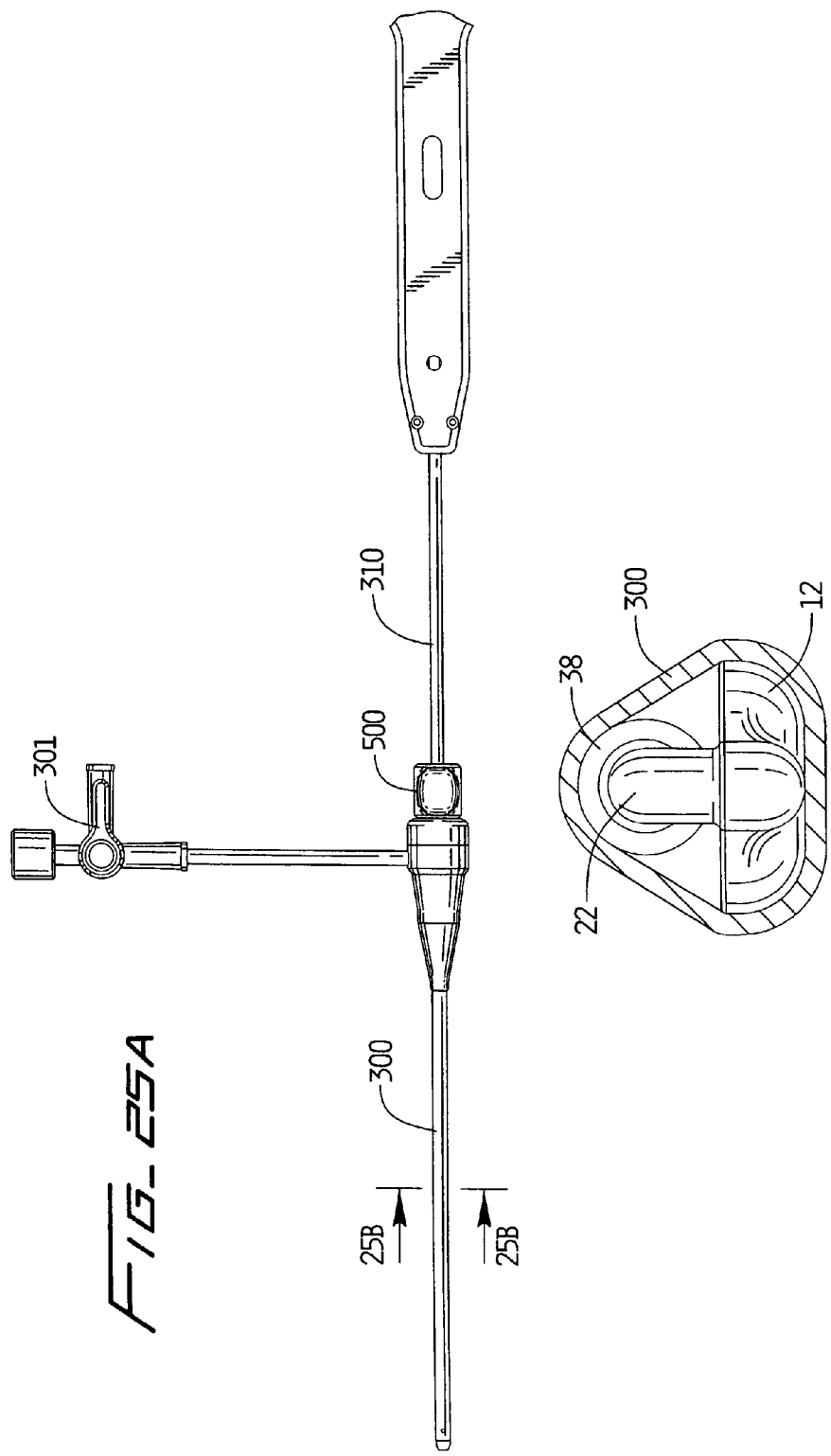

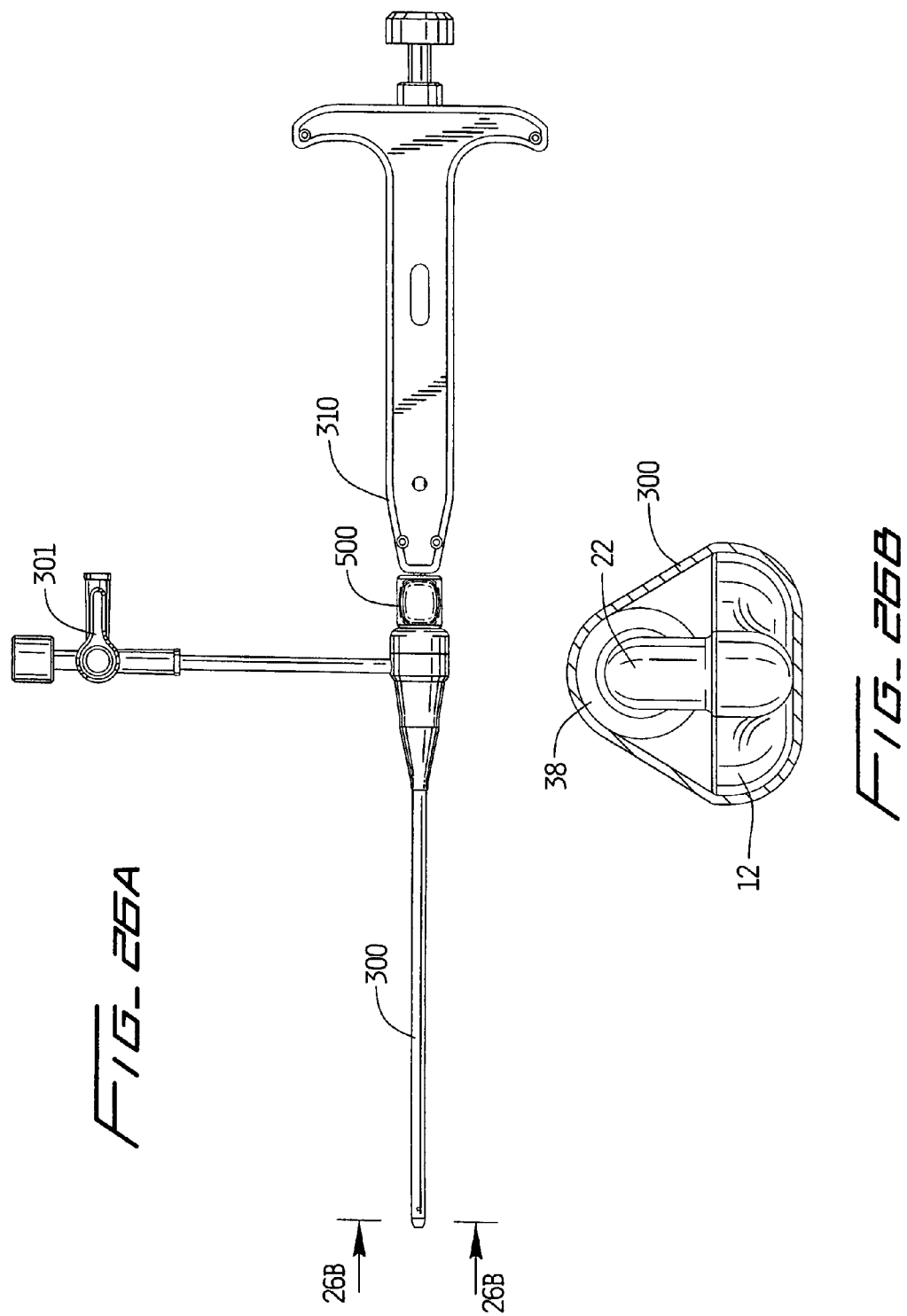

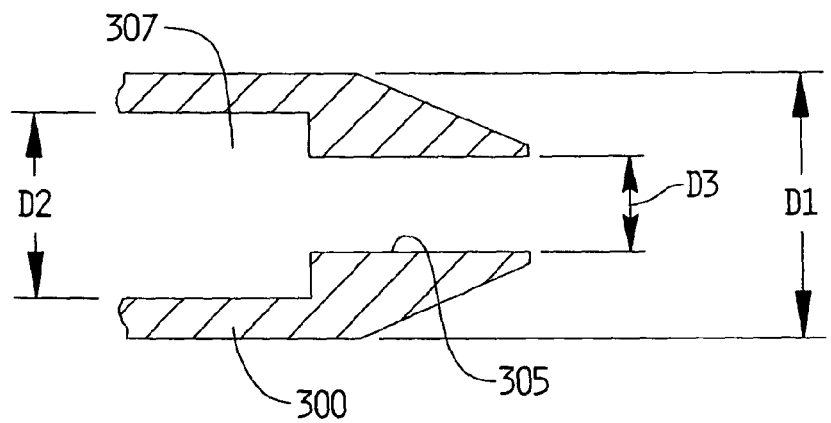
FIG_26C
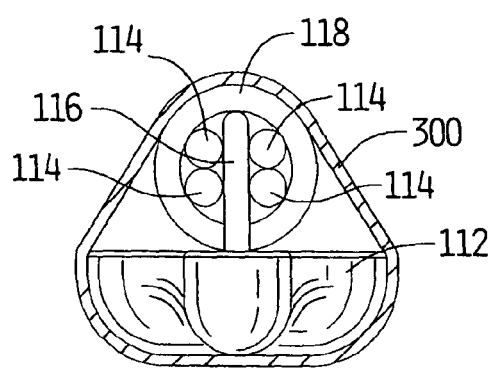
FIG_26D

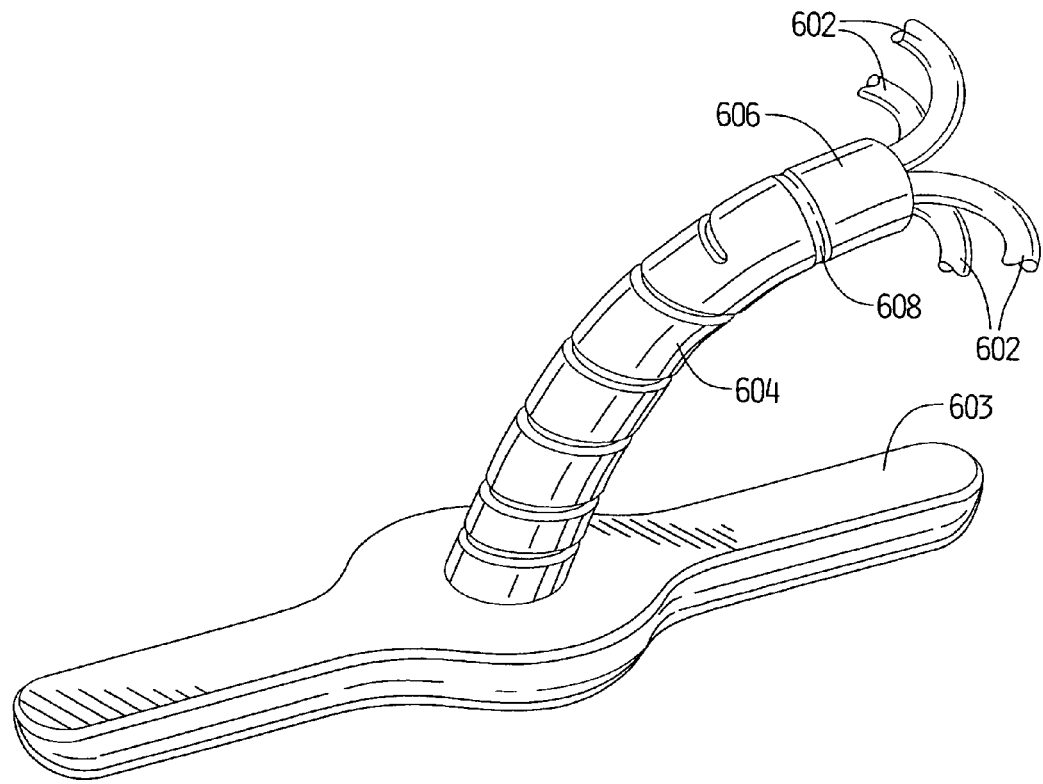
FIG_27A
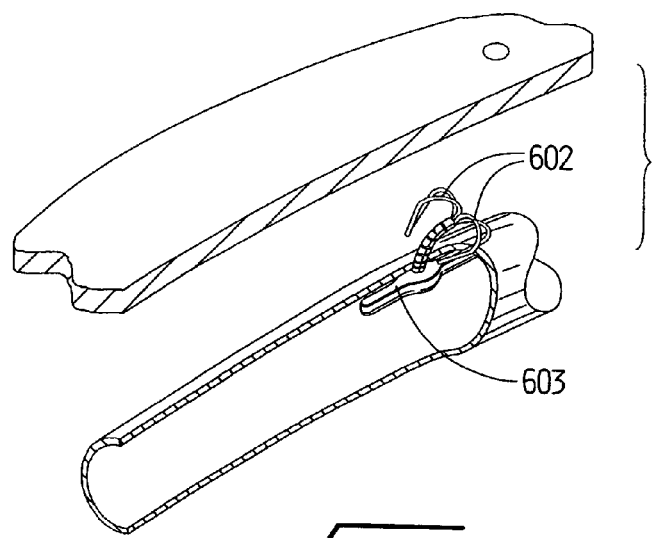
FIG_27B

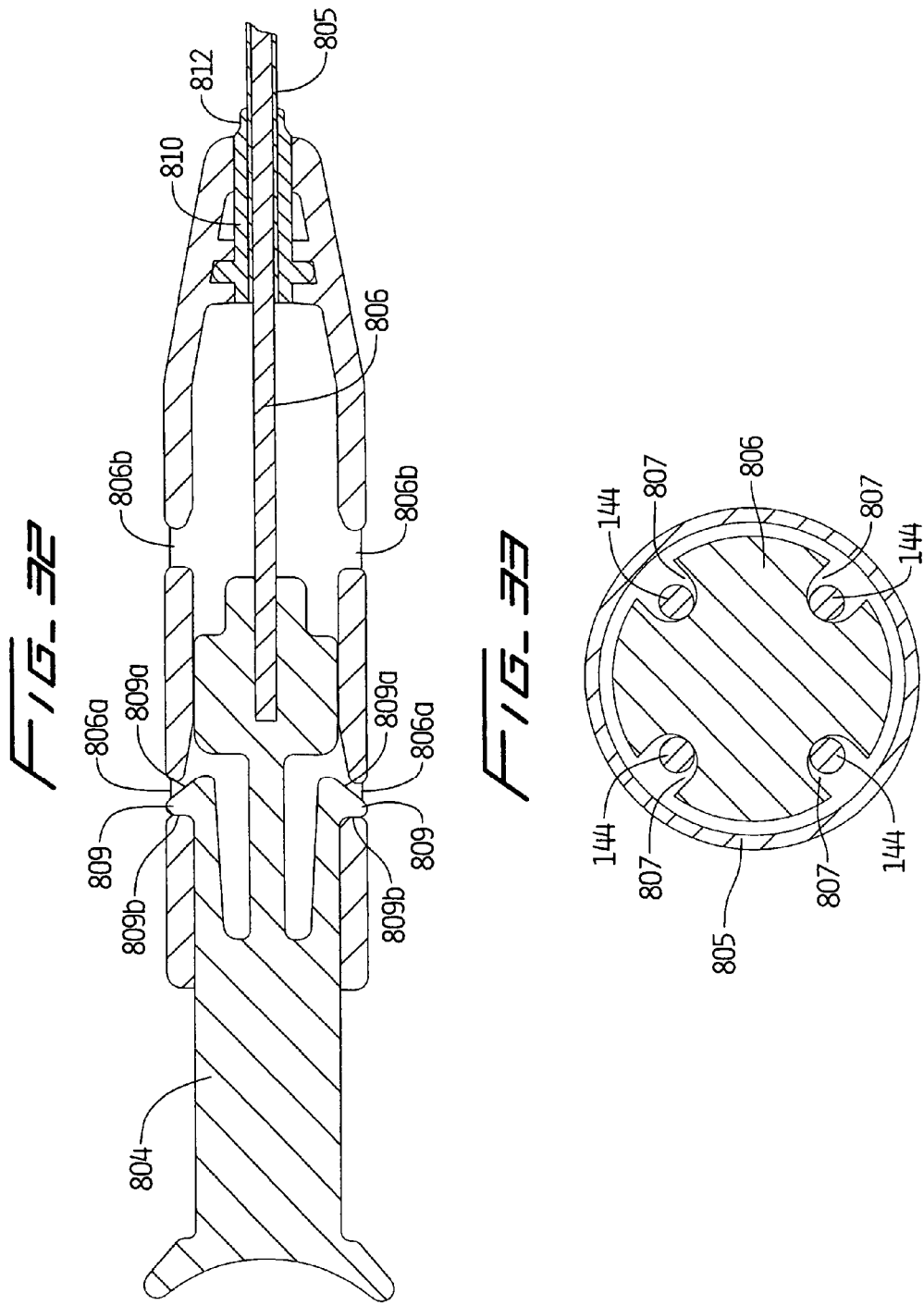

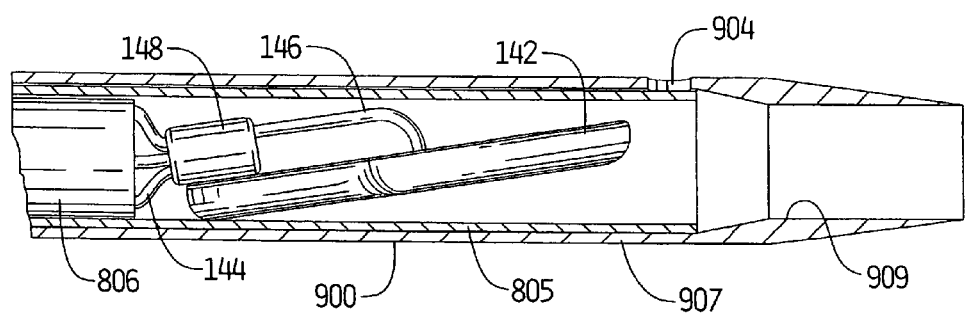
FIG_35
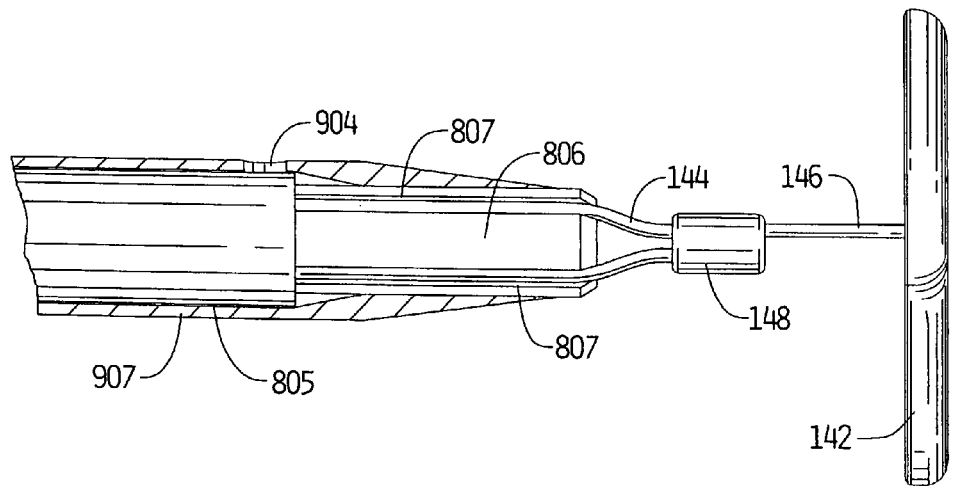
FIG_36

VASCULAR HOLE CLOSURE DEVICE

This application is a continuation of U.S. patent application Ser. No. 10/345,533, filed Jan. 16, 2003, now U.S. Pat. No. 7,267,679, which is a continuation-in-part of U.S. patent application Ser. No. 10/163,142, filed Jun. 5, 2002, now U.S. Pat. No. 7,341,595, which claims priority from provisional application Ser. No. 60/355,526, filed Feb. 6, 2002 and is a continuation-in-part of application Ser. No. 10/846,801, filed May 14, 2004, now U.S. Pat. No. 7,662,168, which is a continuation of application Ser. No. 10/269,899, filed Oct. 11, 2002, now U.S. Pat. No. 6,749,622, which is a continuation of application Ser. No. 09/659,648, filed Sep. 12, 2000, now abandoned, which claims priority from provisional patent application Ser. No. 60/153,736, filed Sep. 13, 1999. The contents of each of these applications is incorporated herein by reference in their entirety.

BACKGROUND

1. Technical Field

This application relates to a vascular device and more particularly to a device for closing openings in vessel walls.

2. Background of Related Art

During certain types of vascular surgery, catheters are inserted through an incision in the skin and underlying tissue to access the femoral artery in the patient's leg. The catheter is then inserted through the access opening made in the wall of the femoral artery and guided through the artery to the desired site to perform surgical procedures such as angioplasty or plaque removal. After the surgical procedure is completed and the catheter is removed from the patient, the access hole must be closed. This is quite difficult not only because of the high blood flow from the artery, but also because there are many layers of tissue that must be penetrated to reach the femoral artery.

Several approaches to date have been used to close femoral access holes. In one approach, manual compression by hand over the puncture site is augmented by a sandbag or weight until the blood coagulates. With this approach, it can take up to six hours for the vessel hole to close and for the patient to be able to ambulate. This inefficiency increases the surgical procedure time as well as the overall cost of the procedure since the hospital staff must physically maintain pressure and the patient's discharge is delayed because of the inability to ambulate.

In another approach to close the vessel puncture site, a clamp is attached to the operating table and the patient's leg. The clamp applies pressure to the vessel opening. The patient, however, must still be monitored to ensure the blood is coagulating, requiring additional time of the hospital staff and increasing the cost of the procedure.

To avoid the foregoing disadvantages of manual pressure approaches, suturing devices have been developed. One such suturing device, referred to as "the Closer" and sold by Perclose, advances needles adjacent the vessel wall opening and pulls suture material outwardly through the wall adjacent the opening. The surgeon then ties a knot in the suture, closing the opening. One difficulty with the procedure involves the number of steps required by the surgeon to deploy the needles, capture the suture, withdraw the suture, and tie the knot and secure the suture. Moreover, the surgeon cannot easily visualize the suture because of the depth of the femoral artery (relative to the skin) and essentially ties the suture knot blindly or blindly slips a pre-tied knot into position. Additionally, the ability to tie the knot varies among surgeons; therefore success and accuracy of the hole closure can be dependent on the skill of the surgeon. Yet another disadvantage of this suturing instrument is that the vessel opening is widened for insertion of the instrument, thus creating a bigger opening to close in the case of failure to deliver the closure system. It is also difficult to pass the needle through calcified vessels.

U.S. Pat. No. 4,744,364 discloses another approach for sealing a vessel puncture in the form of a device having an expandable closure member with a filament for pulling it against the vessel wall. The closure member is held in place by a strip of tape placed on the skin to hold the filament in place. However, the closure device is still subject to movement which can cause leakage through the puncture. Additionally, if the suture becomes loose, the closure member is not retained and can flow downstream in the vessel. Moreover, since the suture extends through the skin, a potential pathway for infection is created. The closure device in U.S. Pat. No. 5,545,178 includes a resorbable collagen foam plug located within the puncture tract. However, since coagulation typically takes up to twenty minutes and blood can leak in between the plug and tissue tract, manual pressure must be applied to the puncture for a period of time, until the collagen plug expands within the tract.

It would therefore be advantageous to provide a device which would more quickly and effectively close openings (punctures) in vessel walls. Such device would advantageously avoid the aforementioned time and expense of applying manual pressure to the opening, simplify the steps required to close the opening, avoid widening of the opening, and more effectively retain the closure device in the vessel.

SUMMARY

The present invention overcomes the disadvantages and deficiencies of the prior art. The present invention provides a device for closing an aperture in a vessel wall comprising an elongated member having a longitudinal axis, positionable inside the vessel against the internal opening of the aperture, and having a dimension at least substantially equal to a dimension of the internal opening of the aperture to prevent egress of fluid through the aperture. At least two curved legs, curved in different directions, are formed from a single element of metallic material and positionable outside the vessel to help retain the elongated member in position.

The at least two curved legs may be composed of shape memory material. The metallic element in one embodiment is formed to separate at a first end into curved leg regions and further formed with a tab at a second end to couple the curved legs to the elongated member. The elongated member can have a slot formed therein to receive the tab. The elongated member can be oval shaped with a substantially uniform width between first and second end portions may be composed of a resorbable material. The elongated member can have a thickness at a central portion greater than a thickness at an end portion.

In one embodiment, the legs curve in a direction substantially parallel to the longitudinal axis of the elongated member. In another embodiment the legs curve in a direction substantially perpendicular to the longitudinal axis of the elongated member.

The present invention also provides a device for closing an aperture in a vessel wall comprising an elongated member having a longitudinal axis and a transverse axis and positionable inside the vessel against the internal opening of the aperture, wherein the elongated member has a dimension at least substantially equal to a dimension of the internal opening of the aperture to prevent egress of fluid through the aperture. At least two curved legs are connected to the elongated member and positionable outside the vessel to help retain the elongated member in position wherein the legs curve in a direction substantially perpendicular to the longitudinal axis of the elongated member.

The elongated member may have a U-shaped channel formed therein to receive the legs. The elongated member can be oval shaped with a substantially uniform width between first and second end portions and can be composed of a resorbable material. In one embodiment, the central portion of the elongated member has a thickness greater than an end portion. The legs may be composed of a shape memory material. An end portion and/or curved portion of the legs may extend beyond the widthwise dimension of the elongated member.

The present invention also provides a device for closing an aperture in a vessel wall comprising an elongated member having a longitudinal axis and positionable inside the vessel against the internal opening of the aperture, wherein the elongated member has a dimension at least substantially equal to a dimension of the internal opening of the aperture to prevent egress of fluid through the aperture. At least two curved legs, curved in different directions, are connected to the elongated member at an acute angle and positionable outside the vessel to help retain the elongated member in position.

BRIEF DESCRIPTION OF THE DRAWINGS

Preferred embodiment(s) of the present disclosure are described herein with reference to the drawings wherein:

FIG. 1 is a perspective view of a first embodiment of the closure device of the present invention showing the clip legs in their memorized position;

FIG. 2 is a bottom view of the closure device of FIG. 1;

FIGS. 3-5 are front views of the closure device of FIG. 1 (the suture not shown for clarity) showing movement of the clip legs to their memorized position wherein:

FIG. 3 shows the clip legs in a partially deflected (curved) position;

FIG. 4 shows the clip legs in a further deflected position; and

FIG. 5 shows the clip legs in their memorized position;

FIG. 6 is a side view illustrating the closure device of FIG. 1 partially deployed from the introducer sheath wherein the elongated member is retained in a longitudinal position;

FIG. 7 is a view similar to FIG. 6 except showing the closure device further deployed from the introducer sheath to enable the elongated member to rotate to its transverse position;

FIG. 8 is a transverse cross-sectional view showing the positioning of the connecting wire and the clip legs within the collar of the closure device;

FIG. 9A is a perspective view of a second embodiment of the closure device of the present invention having an alternately configured elongated member;

FIG. 9B is a perspective view of a third embodiment of the closure device of the present invention having a paddle shaped elongated member;

FIG. 9C is an exploded view of the closure device of FIG. 9B;

FIG. 9D is a side view of the closure device of FIG. 9B;

FIG. 9E is a transverse cross-sectional view showing the positioning of the connecting wire and clip legs of FIG. 9B within the collar of the closure device;

FIG. 10A is a perspective view of a fourth embodiment of the closure device of the present invention having clip legs formed of independent flat wire sections;

FIG. 10B is a perspective view of a fifth embodiment of the closure device of the present invention having clip legs integrally formed from rectangular tubing;

FIG. 10C is a perspective view of a sixth embodiment of the closure device;

FIGS. 10D and 10E are respective exploded and side views of the closure device of FIG. 10C;

FIG. 10F is a perspective view of a seventh embodiment of the closure device of the present invention;

FIGS. 10G and 10H are respective exploded and top views of the closure device of FIG. 10F;

FIG. 10I is a cross-sectional view taken along lines I-I of FIG. 10H;

FIG. 10J is a perspective view of an eighth embodiment of the closure device of the present invention;

FIGS. 10K and 10L are respective exploded and top views of the closure device of FIG. 10J;

FIGS. 10M and 10N are cross-sectional views taken along lines M-M and N-N, respectively, of FIG. 10L;

FIG. 11A is a perspective view of a ninth embodiment of the closure device of the present invention having a connecting wire extending through an eyelet of the elongated member;

FIG. 11B is a perspective view of a tenth embodiment of the closure device of the present invention having a connecting wire insert molded in the elongated member;

FIG. 11C is a perspective view of an eleventh embodiment of the closure device of the present invention having flattened clip legs with a retaining mechanism engagable with the collar;

FIG. 11D is a schematic representation of an elongated member with varying regions of resorbability;

FIGS. 12A-12E are perspective views, with a portion of the vessel cut away, illustrating a first method of delivery of the closure device of FIG. 1 wherein:

FIG. 12A shows the dilator and sheath inserted over the guidewire into the target vessel;

FIG. 12B shows the delivery instrument positioned within the introducer sheath inserted through the skin opening and through the vessel wall aperture into the interior of the vessel;

FIG. 12C illustrates the elongated member of the closure device advanced beyond the distal end of the introducer sheath into the vessel lumen;

FIG. 12D illustrates the closure device pulled proximally so the elongated member abuts the internal wall of the vessel to cover the internal opening of the aperture; and FIG. 12E illustrates the introducer sheath and delivery instrument being fully withdrawn to fully deploy the closure device so the clip legs move toward their memorized position to engage the tissue;

FIG. 12F is a side view showing the introducer sheath extending through the internal and external openings of the vessel wall aperture;

FIGS. 13A-13E are perspective views, with a portion of the vessel cut away, illustrating an alternate method of delivery of the closure device of FIG. 1 wherein:

FIG. 13A shows the dilator and sheath being inserted over the guidewire into the target vessel;

FIG. 13B shows the delivery instrument positioned within the introducer sheath inserted through the skin opening and through the vessel wall aperture into the interior of the vessel to a position where it is desirable to deploy the elongated member;

FIG. 13C illustrates the introducer sheath withdrawn proximally in a slot in the delivery instrument to release the elongated member of the closure device into the vessel;

FIG. 13D illustrates the closure device pulled proximally so the elongated member abuts the internal wall of the vessel to cover the internal opening of the aperture; and FIG. 13E illustrates the introducer sheath and delivery instrument being fully withdrawn to fully deploy the closure device so the clip legs move toward their memorized position to engage the tissue;

FIG. 14 is a perspective view similar to FIGS. 12D and 13D showing the closure device partially deployed so that the elongated member is in its transverse position against the internal wall of the vessel;

FIG. 15 is an enlarged perspective view of the region of the closure device outlined in FIG. 14;

FIG. 16A is a perspective view of a twelfth embodiment of the closure device of the present invention placed by a delivery instrument having a slotted tube overlying the collar;

FIG. 16B is a perspective view of the slotted tube of FIG. 16A;

FIG. 16C is a transverse cross-sectional view taken through the collar of FIG. 16A;

FIG. 16D is a perspective view of an alternate delivery instrument of the present invention for placement of the closure device, the instrument having a pair of jaws engaging the collar (the clip legs removed for clarity);

FIG. 17A is a front view of a thirteenth embodiment of the closure device of the present invention having a mushroom shaped aperture covering member;

FIG. 17B is a side view of the closure device of FIG. 17A;

FIG. 18 is a side view of another alternate embodiment of the delivery instrument for the closure device having a projecting tip for pivoting the elongated member;

FIG. 19 is a side view of the closure device of FIG. 15 with the delivery instrument of FIG. 18;

FIG. 20 is a side view of a fourteenth embodiment of the closure device of the present invention having a wire offset with respect to the elongated member for biasing the elongated member to the transverse position;

FIG. 21 is a perspective view of yet another alternate embodiment of the delivery instrument for the closure device of the present invention having a pair of jaws for grasping and releasing the closure device;

FIG. 22 is an enlarged view of the region outlined in FIG. 21 showing the jaws grasping the closure device;

FIG. 23A is a perspective view of an insertion tube configured for insertion into the introducer sheath;

FIG. 23B is a longitudinal cross-sectional view of the insertion tube positioned within the introducer sheath;

FIG. 25A is a side view similar to FIG. 24A except showing the delivery instrument inserted further into the introducer sheath;

FIG. 25B is a view taken along lines B-B of FIG. 25A showing the introducer sheath in cross section and the closure device positioned therein deflecting the sheath;

FIG. 26A is a side view similar to FIG. 24A except showing the delivery instrument fully inserted into the introducer sheath;

FIG. 26B is a cross-sectional view taken along lines B-B of FIG. 26A showing the closure device positioned therein and deflecting the sheath;

FIG. 26C is a cross-sectional view of the distal end of the introducer sheath of FIG. 26A;

FIG. 26D is a cross-sectional view similar to FIG. 26B except showing the closure device of FIG. 11B positioned in the introducer sheath;

FIG. 27A is a perspective view of a fifteenth embodiment of the closure device of the present invention having a spiral tube;

FIG. 27B is a perspective view of the closure device of FIG. 27A positioned to close the aperture in the vessel wall;

FIG. 32 is a cross-sectional view of the proximal end of the delivery instrument of FIG. 31 showing the plunger in the retracted position;

FIG. 33 is a transverse cross-sectional view taken along lines C-C of the delivery instrument of FIG. 31 (with the introducer sheath removed for clarity);

FIG. 35 is a side view illustrating the distal end of the delivery instrument and the closure device in the introducer sheath;

FIG. 36 is a side view showing the elongated member advanced from the delivery instrument and introducer sheath by the pusher;

DETAILED DESCRIPTION OF PREFERRED EMBODIMENTS

Figure 13A:
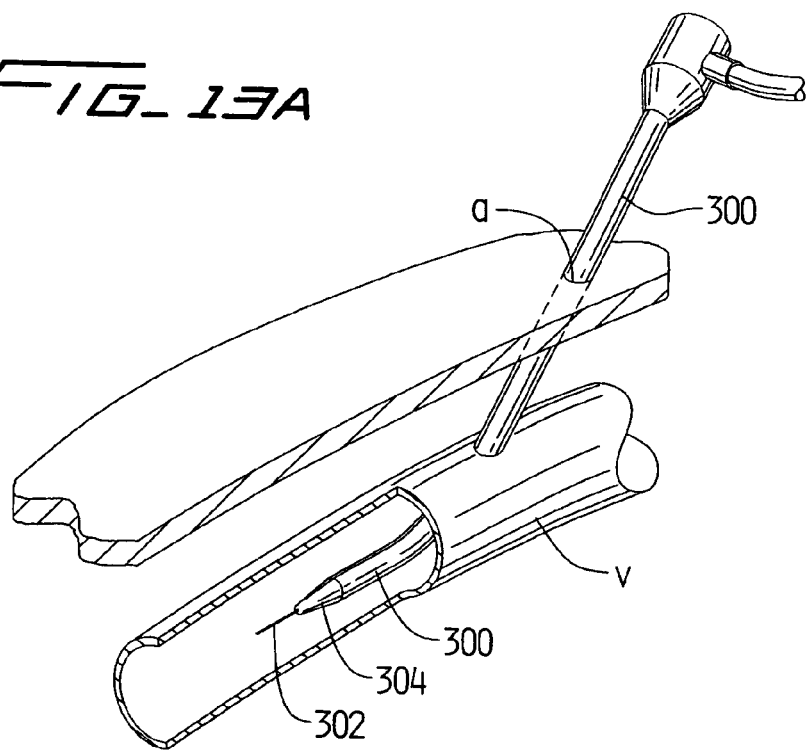

Referring now in detail to the drawings where like reference numerals identify similar or like components throughout the several views, FIG. 1 is a perspective view of first embodiment of the vascular hole (aperture) closure device of the present invention. The device is intended to close an aperture in the vessel wall, typically formed after removal of a catheter previously inserted through the vessel wall into the vessel lumen for performing angioplasty or other interventional procedures. The aperture extends through the patient's skin and underlying tissue, through the external wall of the vessel, through the wall of the vessel, and through the internal wall of the vessel to communicate with the internal lumen of the vessel. The closure devices of the present invention have a covering member or patch positioned within the vessel pressing against the internal wall of the vessel to block blood flow and a clip positioned external of the vessel wall to retain the covering member. The clip pulls the covering member upwardly towards the aperture.

Turning first to FIGS. 1-5, a first embodiment of the closure device of the present invention is illustrated. Hole (aperture) closure device 10 has an elongated member 12 and a clip 14 having four legs, preferably in the form of wires, 30a, 30b, 30c, and 30d retained within a collar 38. The elongated member 12 is dimensioned and configured for positioning inside the vessel on the internal side of the aperture; the wires 30a-30d are configured to be positioned outside the vessel wall adjacent the external side of the aperture.

Elongated member 12 is retained in a longitudinal position for delivery to the vessel, and then pivots to a transverse position within the vessel lumen. This movement is illustrated in FIGS. 6 and 7 wherein elongated member 12 is partially deployed from the introducer sheath 300, but still retained in a longitudinal position by engagement of the wall at distal end 303 (FIG. 6) with end region 18. When fully deployed from the introducer sheath 300, end region 18 of elongated member 12 is also released so it can pivot to the transverse position of FIG. 7 where it's substantially perpendicular to an axis extending through the aperture. Note that preferably the center of collar 38 is slightly offset from the eyelet 24, enabling the elongated member 12 to pivot slightly when deployed; the vessel wall can then further pivot the elongated member to a transverse position as it is pulled back against the wall. This movement is described in more detail below in conjunction with the discussion of the method of insertion of closure device 10. The legs 30a-30e of the clip 14 are retained in a substantially straightened position for delivery and when released moved to a curved configuration. This is also discussed in detail below.

The elongated member 12 functions to cover (patch) the internal opening in the vessel wall to prevent the egress of blood. As illustrated in FIGS. 1 and 2, the elongated (covering) member has an enlarged region 20 between the first and second end regions 16, 18. The longitudinal axis defines a lengthwise dimension L and transverse axes define widthwise dimensions. The widthwise dimension w1 at the ends 16 and 18 of the elongated member 12 are preferably substantially equal and preferably range from about 0.025 inches to about 0.035 inches. At the enlarged region 20, the widthwise dimension progressively increases, so its maximum width w2 preferably ranges from about 0.090 inches to about 0.125 inches. This central enlarged region 20 of elongated member 12 provides a larger area to patch (cover) the internal opening in the vessel. The width w2 preferably is at least substantially equal to the dimension of the internal opening to effectively cover the opening. Other dimensions are also contemplated.

It should be appreciated that the elongated member could be provided without an enlarged region as long as it has sufficient area to cover the opening (aperture). This is illustrated by way of example in FIG. 9A, wherein closure device 50 has an elongated member 60 which is substantially uniform in width throughout its length. In this embodiment, connecting wire 56 abuts projecting surface 62 of elongated member 60 to tip (pivot) the elongated member 60. In all other respects, closure device 50 is identical to device 10, e.g. four legs 52a, 52b, 52c and 52d retained within a collar 59 and connected to elongated member 60 by connecting wire 56 extending through the opening in projecting surface 62.

The elongated member could also be configured asymmetrically so that the enlarged region is off centered to accommodate widening of the aperture as the member is pulled at an angle. The elongated member can also be configured in a paddle shape with a narrowed region adjacent a wider region as discussed below in conjunction with FIGS. 9B-9E.

The elongated member can be composed of materials such as polycarbonate or polyurethane, or alternatively can be composed of resorbable materials such as glycolide/lactide polymers which after a period of time resorbs in the body, leaving only the clip portion external of the vessel lumen. If composed of resorbable material, the elongated member could optionally have regions of varying resorbability. One example is shown in FIG. 11D, where region R1 would be the last to resorb, region R2 would resorb at a slower rate, and Region R3 would be the first to resorb. One of more of these regions, e.g. R1 and R2, could optionally not be resorbable. Varying degrees of resorbability can be achieved by utilizing different materials having differing resorbable characteristics or by varying the thickness of the regions of the elongated member (the thicker regions taking a longer time to resorb).

With continued reference to the closure device 10 of FIGS. 1-5, the elongated member 12 has an opening or eyelet 24 formed in projecting surface 22. Opening 24 receives a connecting wire 40 to couple the clip 14 to the elongated member 12. The clip legs 30a-30d of clip 14 each have a first portion which extends through collar 38, terminating at ends 33a-33d, respectively, and a second end 32a-32d, respectively, which is configured to engage tissue. In FIG. 1, the ends 32a-32d are non-penetrating blunt tips. However, it is also contemplated that sharpened or tissue penetrating tips could alternatively be provided. The clip legs 30a-30d are retained in the collar 38 by laser welding, glue, or other securing means. Alternatively, the clip legs can be welded or otherwise attached to each other (and the connecting wire) without the need for a collar.

Also fixed within collar 38, by any suitable means, e.g. laser welding or glue, is connecting wire 40 which loops at region 42 through opening 24. The two ends of the connecting wire are designated by reference numeral 44. (Only one end is shown). FIG. 8 illustrates a transverse cross-sectional view taken through collar 38 to illustrate the positioning of the clip legs 30a-30d and connecting wire 40 within the collar 38. Suture 45 also extends through eyelet 24 and functions to position the elongated member 12 as described in detail below.

Clip legs 30a, 30b, 30c, and 30d are preferably composed of four discrete wire elements composed of shape memory material, such as Nitinol (nickel titanium alloy) with a memorized position of that shown in FIG. 5. In use, the clip legs 30a-30d are retained in the delivery instrument in a substantially straightened position, and when released, are warmed by body temperature to curve inwardly as shown in FIGS. 3 and 4. The extent to which the clip legs can return to their memorized position will depend on the thickness and resistance of the tissue. Once curved inwardly, the curved clip legs 30a-30d grasp the tissue to retain the closure device 10 within the tissue. As the legs 30a-30d curve inwardly, they apply a proximal pulling force on the elongated member 12 to pull it slightly upwardly (proximally) against the vessel wall. The legs may gather and force tissue on the external side of the vessel wall toward the opening.

FIG. 10A illustrates an alternate embodiment of the closure device of the present invention, designated by reference numeral 70. Closure device 70 is similar to closure device 10 except for the shape of the clip legs 78 (only two of which are shown) and the collar 75. Clip legs 78 (preferably four are provided) are made of wire having a rectangular cross-sectional shape. The clip legs 78, as shown, are formed into an elongated U-shape. Also, instead of the cylindrical collar 38 of closure device 10, a rectangular shaped collar 75 is provided. In all other respects, e.g. elongated covering member 72, connecting wire 73, etc. closure device 70 is identical to closure device 10.

In the embodiment of FIG. 10B, the clip legs 84a-84d of closure device 80 are initially formed from rectangular (or square) tubing. As shown, tubing 86 is split, preferably by laser cutting to form the four curved legs 84a-84d which in their closed position form a C-shape configuration. Elongated covering member 85 is identical to elongated member 12 of closure device 10 with an enlarged width region 85 for covering (patching) the internal side of the opening. A connecting wire 83 connects the clip portion to the elongated member via eyelet 88. Plug 87 is slip fit over connecting wire 83 and has one or more tabs 89 snap fit through window 86a in tubing 86 to connect the elongated member 82 to the tubing 86.

It should be appreciated that the other embodiments disclosed herein could also have retaining tabs for attachment to the collar portion.

In the embodiment of FIGS. 10C-10E, the closure device 270 has two clip legs 272a, 272b formed from a single sheet or strip of metallic material such has shape memory material, e.g. Nitinol. Alternatively more than two legs, e.g. four legs, can be formed from the metallic material. The clip legs 272a, 272b, curved into a C-shape as shown, separate at central region 274 to curve in opposite directions. This splitting at the central region and formation of the clip legs is preferably done by laser cutting a rectangular tubing. Central region 274 has a reduced width area 276. The connecting end is curved to form a hook or tab 278 for attachment to the elongated member (patch) 280. The connecting end also includes a reduced width portion 279 to form a shoulder for mechanical securement of the tab 278 within the elongated member 280.

Elongated member 280, as shown, is oval shaped with elongated parallel side walls 282a, 282b and arcuate end walls 284a, 284b connecting the side walls 282a, 282b. In this configuration of the elongated member 280, other than the end portions, the width z is substantially uniform. The transverse slot or opening 285 is configured to receive the tab 278 for securement of the clip legs to the elongated member 280. To enhance securement, during manufacture the elongated member is preferably heated to melt around the tab. Other securement processes are also contemplated.

It is also contemplated that the closure device 280 can be formed with the two clip legs positioned with respect to the elongated member 90 degrees out of phase from FIG. 10C. That is, the slot in the elongated member would be oriented longitudinally and the tab directed transversely (or else the legs twisted at a 9o degree angle with respect to the longitudinal tab) such that the clip legs 272a, 272b would curve in a direction substantially perpendicular to the longitudinal axis of the elongated member rather than in a direction substantially parallel to the longitudinal axis as in FIG. 10C. Such orientation would reduce the profile of the clip along the length of the vessel to enable positioning multiple clips along the vessel closer to one another. An example of such orientation of the clip legs with respect to the elongated member is illustrated in the embodiment of FIG. 10J described below.

FIGS. 10F-10I illustrate another embodiment of a collarless clip closure design. In this embodiment, the elongated member (patch) 380 of closure device 370 is shaped similar to elongated member 280 of the FIG. 10C embodiment in that it is oval shaped and of substantially uniform width y except for its end portions 385, 387. The elongated member has a central portion with a thickness "k" at a central portion greater than the thickness at the end portions. This results in the end portions resorbing at a faster rate than the central portion, the region which attaches to the clip portion so that the clip attachment remains longer. Elongated member 380 has two openings 384, 386 on its upper surface 388 and a longitudinally extending groove 389 on its lower surface 390, together forming a U-shaped channel for receipt of the clip.

The clip portion, as shown, comprises a round wire bent to form two clip legs 371, 372 positioned 180 degrees apart. The clip legs 371, 372 curve outwardly in a direction substantially parallel to the longitudinal axis of the elongated member 380. Clip leg 371 has a tip 371a, a curved portion 371b and a straight portion 371c. Clip leg 372 has a tip 372a, a first curved portion 372b, a second curved portion 372c, and straight portion 372d. The straight portions 371c, 372d of the clip legs 371, 372 are joined by longitudinally extending portion 373. This portion 373 is seated within groove 389 in lower surface 390 of elongated member 380. Straight portions 371c, 372d extend through openings 384, 386 of elongated member 380. To enhance securement of the clip portion to the elongated member 380, during manufacture the elongated member can be heated to melt the plastic around the clip. During delivery of the clip to the surgical site, the clip legs would be folded on top of the elongated member 380 to the left as viewed in FIG. 10F, with the curved portion 372c facilitating such bending.

In the alternate embodiment of FIGS. 10J-10N, the clip legs are oriented to curve in a direction substantially perpendicular to the longitudinal axis of elongated member (patch) legs 471, 472 of closure device 470 each have a respective tip 471a, 472a, a curved portion 471b, 472b, a straight portion 471c, 472c, a diverging leg portion 471d, 472d, and a lower straight portion 471e, 472e connected by transverse portion 474. Note a portion of the legs, e.g. the tips 471a, 471b and a curved portion, exceed the widthwise dimension of the elongated member 480. The clip legs extend into the U-channel in the elongated member 480 formed by openings 484, 486 and transverse groove 488. The transverse positioning of the clip legs results in the clip occupying less space along the vessel when implanted, thereby allowing placement of additional clips closer together at a later time, e.g. after the resorbable elongated member is resorbed. The clip portion is also positioned at an acute angle "b" such as 45 degrees (other angles are also contemplated) to the elongated member 480, as shown, so that when inserted in the vessel, the elongated member will emerge substantially parallel to the vessel wall. To achieve this angle, the lower straight portion 471e, 472e extend in a plane substantially perpendicular to the upper surface plane of the elongated member 480 and the straight portions 471c, 472c extend at an acute angle thereto.

Although the straight portions of the clip legs are shown side by side, it is also contemplated that the straight portions could be superimposed.

During delivery, the clip legs 471,472 would fold onto the elongated member, thereby reducing the clip delivery profile. During assembly, the clip can be preloaded so the legs crossover which could enhance the stability to control the deployed orientation of the elongated member. As in the other embodiments of FIG. 10, the elongated member is preferably composed of resorbable material and the clip legs preferably of shape memory material, although other materials are contemplated.

FIG. 11A is a perspective view of another alternate embodiment of the closure device. In this embodiment, closure device 90 has four legs 94 (only two of which are shown) as in the embodiment of FIG. 1. Instead of a suture extending through the eyelet 24 as shown in FIGS. 1 and 14, suture 97 is connected to the loop 95 of connecting wire 96. That is, connecting wire 96 is looped through eyelet 93 of elongated member 92 at one end and receives a suture loop 95 at the opposite end. In this manner, as the suture is pulled proximally, the elongated member (and clip) are pulled proximally. Connecting wire 96 is preferably attached within collar 98 by laser welding, gluing, or other suitable means. Connecting wire 96 can be utilized to bias the elongated member to a transverse position.

In the FIG. 11B embodiment, the connecting wire 116 of closure device 110 is embedded, e.g. insert molded, within the elongated member 112. This reduces the profile of the member 112 since the projecting surface (protrusion) as in the FIG. 11A embodiment is eliminated. Also, the connecting wire 116 is made of material, e.g. shape memory metal, which is designed to be in a substantially straightened position, or alternatively in an angled position such as 45°. This configuration biases the elongated member 112 to the transverse position. Otherwise, device 110 is identical to device 90, e.g. legs 114 (only two are shown), suture 117 attached to connecting wire 116, etc.

FIGS. 9B-9E illustrate an alternate embodiment of the closure device, designated by reference numeral 140, having a flexible connecting wire 146 attached to elongated covering member 142 by insert molding, mechanical connection or other suitable means. As shown, connecting wire 146, optionally composed of shape memory material such as Nitinol, is positioned off center of the connecting member 142 to bias it to the transverse position and to facilitate movement of the connecting member 142 to the longitudinal position for delivery to the vessel. The proximal end of connecting wire 146 is attached by suitable means to the collar 148. Four clip legs 144 as in the embodiment of FIG. 1 are provided. The clip legs 144 can have hooked tips 145 as shown which are positioned within and engage collar 148 to facilitate securement therein.

The elongated covering member 142 is paddle shaped having an enlarged region 142a and a narrowed region 142b, thereby reducing its profile so the overall amount of material left in the vessel after placement of the closure device 140 is reduced. Narrowed region 142b can optionally progressively taper starting from the transition with the enlarged region 142a.

In a preferred manufacturing method, the collar 148, clip legs 144 and connecting wire 146 are laser welded together. The connecting wire 146, with tag end 147 is subsequently connected to covering member 142 in the orientation shown. In this preferred attachment method, covering member 142 has a longitudinal slot with interference bumps (not shown) dimensioned to receive the tag end 147 of connecting wire 142. Absorbable or non-absorbable glue could optionally be applied to enhance the attachment of tag end 147 and to provide a seal.

FIG. 11C illustrates another alternate embodiment of the closure device, designated by reference numeral 130. Closure device 130 has clip legs 134a-134d with planar surfaces formed from wire of rectangular cross-section and is preferably composed of shape memory metal. A connecting strap 136, or alternatively a connecting wire like wire 96 of FIG. 11A, extends through eyelet 133 of elongated member 132. Suture 137 is looped through strap 136 for pulling elongated member 132 against the internal opening of the aperture. The clip legs 134a-134d are retained within collar 138 by engagement of a respective tab 139 on each of the legs extending through a respective window 135 on collar 138.

In the closure devices described herein having four discrete wire legs spaced approximately 90 degrees apart, it is also contemplated that fewer legs, e.g. two legs spaced approximately 180 degrees apart or three legs spaced approximately 120 degrees apart, or more than four legs can be provided to achieve the device retention function. Likewise, the two leg versions can be modified to have fewer or more legs. It should be appreciated that in a four clip version, to conserve space, i.e. minimize the size for positioning within the delivery instrument and introducer sheath, the legs need not be symmetrically spaced with respect to one another, but preferably at least the opposing legs would be about 180 degrees apart. (see e.g. FIG. 16C).

Figure 28A:
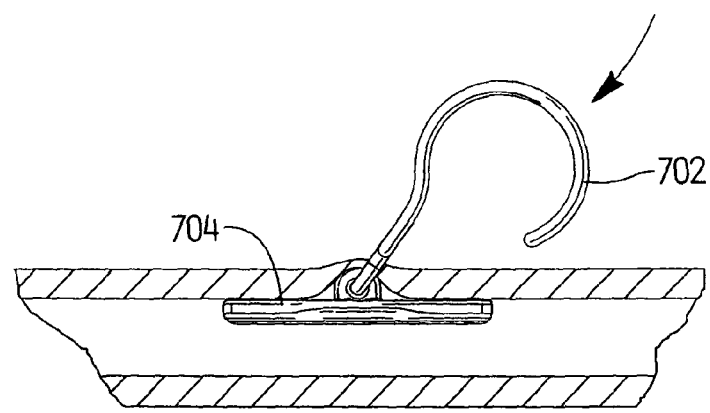
FIG. 28A is a side view of a sixteenth embodiment of the closure device having a single clip leg shown in a deflected position.
Figure 28B:
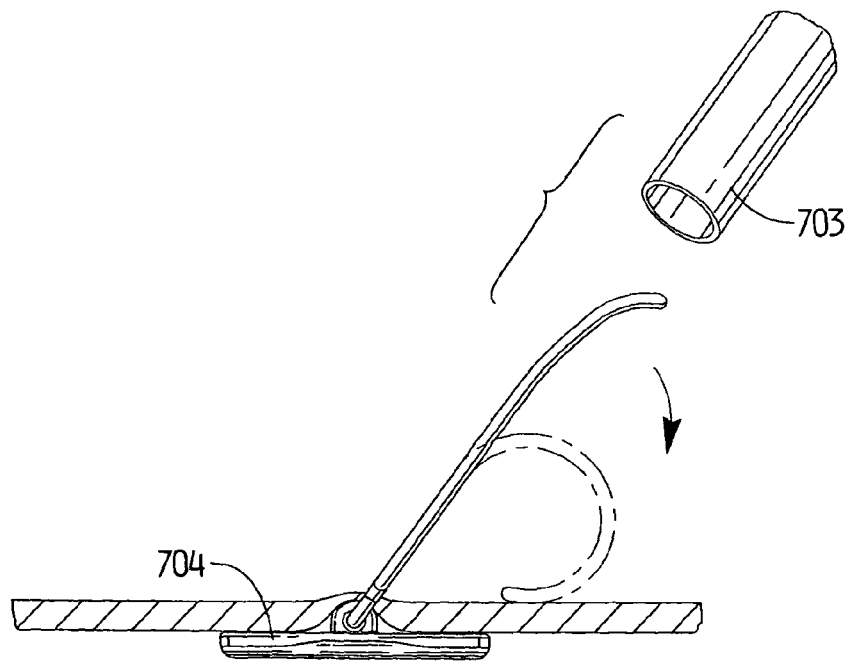
FIG. 28B is a side view of the clip of FIG. 28A showing the range of movement of the clip leg.
Figure 29A:
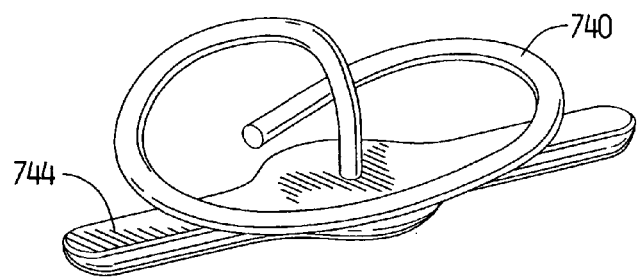
FIG. 29A is a side view of a seventeenth embodiment of the closure device having a single clip leg shown in a partially deflected position.
Figure 29B:
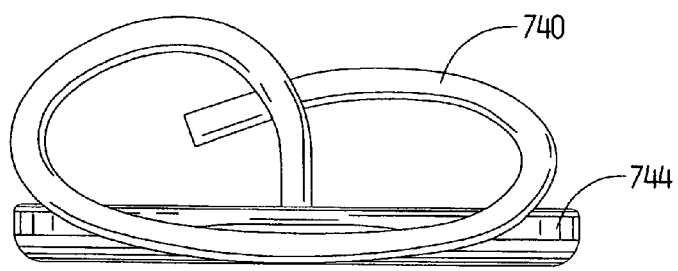
FIG. 29B is a side view of the closure device of FIG. 29A showing the clip leg in a fully deflected position.
Figure 30:
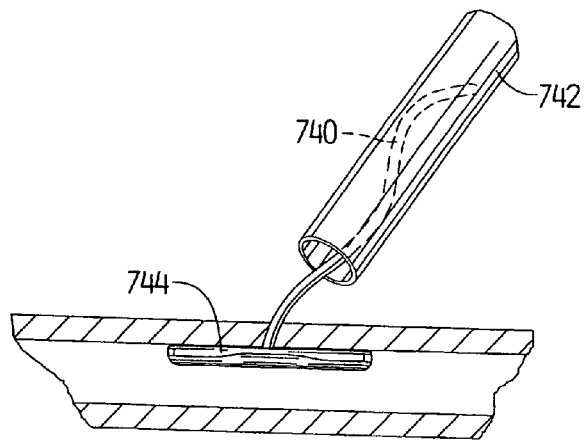
FIG. 30 is a side view of the closure device of FIG. 29A showing the clip leg in the straightened position within the delivery instrument.

FIGS. 28-30 illustrate an example of a single clip leg utilized to retain the elongated member and exert a proximal force on the tissue and elongated member. In FIGS. 28A, 28B, curved clip leg 702, when deployed from delivery instrument 703 curves inwardly as shown to grasp tissue and secure elongated member 704 against the internal vessel wall. In FIGS. 29 and 30, clip leg 740, directly connected to elongated member 744, is retained in a substantially straightened position within the delivery instrument 742 (FIG. 30), and when deployed curves around itself, to form a spring-like element, as shown in FIG. 29B. This clip leg 740 coils to pull up on the elongated member 744 to retain it within the vessel.

In each of the embodiments described herein, blunt or sharpened tips can be provided on the clip legs to perform their gripping function. Although preferably composed of shape memory metal, the clip legs can alternatively be composed of a shape memory plastic, stainless steel, resorbable material, or other materials. It should also be appreciated that the clip legs shown herein represent their full formation, e.g. their memorized position, when formed without any tissue resistance. When placed in tissue, the clip legs would not necessarily move (curve) to the full extent shown. The extent of their curve would depend in large part on the type and thickness of the patient's tissue.

Tuning now to the placement of the closure device of the present invention, FIGS. 12A-12E illustrate a first insertion method. The method illustrated shows placement of closure device 10, however, it should be understood that the other closure devices described herein can be inserted in a similar manner.

As shown in FIG. 12A, a dilator 304 is inserted through introducer sheath 300 and over a guidewire 302 into the vessel lumen. Note the sheath and dilator 304 extend through opening "a" in the skin, through the tissue tract to the vessel V, through external opening "b" in the vessel wall, through the aperture in the vessel wall "w", and through an internal opening "c" on the interior side of the vessel wall into the vessel lumen (see also FIG. 12F).

Next, the guidewire 302 and dilator 304 are withdrawn, and closure applying (delivery) instrument 310 is inserted through the sheath 300 into the vessel lumen as shown in FIG. 12B. The elongated member 12 extends distally of the delivery instrument 310 and is retained in a longitudinal position by the walls of the introducer sheath 300; the clip legs are retained in a substantially straightened position in a martensitic state within the delivery instrument by the infusion of cold saline.

The delivery instrument 310 is advanced through the introducer sheath 300 and past the distal tip 303 so the elongated member 12 is outside the confines of the wall of the introducer sheath 300 and extends into the vessel lumen sufficiently spaced from the internal opening in the vessel wall. This provides sufficient room for pivotal movement of the elongated member 12. As the elongated member 12 is released from the confines of the wall, it is enabled to pivot toward a transverse position as shown in FIG. 12C.

Next, the sheath 300 and delivery instrument 310 are pulled proximally as a unit until the elongated member is seated against the internal opening c in the vessel wall w. (It is contemplated that the sheath 300 and instrument 310 can optionally be fitted (locked) together so they can be moved as a single unit.) Suture 45 extending through eyelet 24 of elongated member 12 (see FIGS. 14 and 15), is attached to the delivery instrument 310 so that pulling the delivery instrument proximally pulls the suture 45 and thus the elongated member 12 proximally. The elongated member 12 is pulled proximally to cover the opening in a patch-like manner with the enlarged region 20 spanning the internal opening c to prevent egress of fluid. Note that the vessel wall further pivots the elongated member to the fully transverse position.

Once elongated member 12 is seated, the closure device is further ejected from the delivery device 310 by distal movement of a pusher (not shown) against the clip legs, thereby forcing clip 14 from the delivery instrument 310 so the clip legs 30a-30d are warmed by body temperature and move towards their memorized configuration. FIG. 12E illustrates the closure device 10 in position with elongated member 12 abutting internal opening c on the internal side of the vessel V to cover (patch) the opening and the retention legs 30a-30d curving downwardly and preferably slightly inwardly towards the tissue tract and aperture to engage the tissue and apply a proximal (upward) force on the elongated member 12. Tissue can also be forced by the curved clip legs 30a-30d towards the aperture and tissue tract on the external side of the vessel wall. FIG. 12E also shows the introducer sheath 300 (and delivery device 310) being withdrawn from the patient's body. The suture is withdrawn with the delivery device 310.

Note that in one embodiment, the suture would be designed to automatically rip when a sufficient load (exceeding a threshold amount) was placed on the suture, thereby separating the closure device from the delivery instrument.

In an alternate insertion method, when the delivery instrument 310 is inserted through the introducer sheath 300, and the elongated member 12 remains within the confines of the wall of the introducer sheath 300 the elongated member is ejected by a pusher rather than by advancement of the delivery instrument. That is, the pusher inside the delivery instrument would be actuated to advance the closure device so the elongated member 12 is moved distally, outside the confines of the introducer sheath wall. In this deployed position of the elongated member 12, the clip legs 30a-30d still remain within the delivery instrument 310 and are not yet deployed. Optionally, the delivery instrument 310 can lock into the sheath 300 at a proximal end. After pulling back on the elongated member 12 to cover the internal opening of the vessel, the clip legs 30a-30d are deployed by moving the delivery instrument 300 proximally to expose the clip legs or by further actuating the pusher to advance the clip legs from the delivery instrument.

FIGS. 13A-13E illustrate an alternate method of insertion of the closure device 10 of the present invention. It should be understood that the other closure devices disclosed herein could also be delivered with delivery instrument 320. The delivery method of FIGS. 13A-13E is the same as the method of FIGS. 12A-12E except that instead of advancing the closure device distally to free the elongated member for pivotal movement, the introducer sheath 300 is retracted with respect to delivery instrument 320.

Figure 13B:
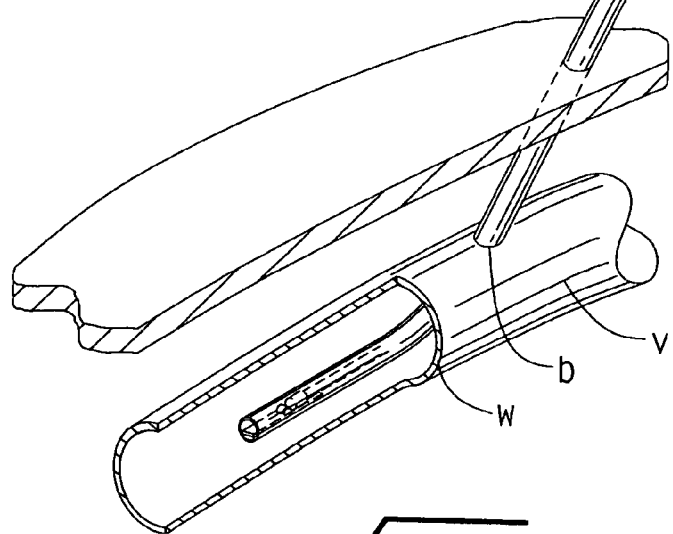

More specifically, in this method, the dilator (FIG. 13A) is introduced over the guidewire in the same manner as FIG. 12A. Note FIG. 13A shows partial introduction as the sheath would be advanced further into the vessel corresponding to the position of FIG. 13B. Note also, the introducer sheath 300 is inserted into the vessel, but further into the vessel than in the method of FIG. 12, as shown in FIG. 13B. That is, the distal tip 303 of the introducer sheath 300 is moved to the position where it is desired to release the elongated member 12 into the vessel. Once in position, the introducer sheath 300 is retracted with respect to the delivery instrument 320, with tubing connector 314 received in a slot 322 of delivery instrument 320. As the sheath 300 is retracted, the elongated member 312 is exposed as shown in FIG. 13C, thus enabling the elongated member 12 to pivot towards its transverse position as it is no longer retained by the wall of the introducer sheath 300. The remaining steps for pulling the elongated member 12 proximally and releasing the clip (illustrated in FIGS. 13D and 13E) are identical to the steps described above with respect to FIGS. 12D and 12E.

To enable movement between an expanded and collapsed configuration in the delivery methods described herein, as noted above, clips legs 30a-30d are preferably made of shape memory metal material, such as Nitinol, a nickel titanium alloy. To facilitate passage of the clip legs through the lumen of the delivery instrument 320 and into the vessel, cold saline is injected into the delivery instrument 320 and around the legs 30a-30d in their collapsed position within the delivery instrument 320. This shape memory material characteristically exhibits rigidity in the austenitic state and more flexibility in the martensitic state. The cold saline maintains the temperature dependent wires 30a-30d in a relatively softer condition as they are in the martensitic state within the delivery instrument. This facilitates the exit of wires 30a-30d from the delivery instrument 320 as frictional contact between the wires 30a-30d and the inner surface of the instrument 320 would otherwise occur if the wires were maintained in a rigid, i.e. austenitic, condition. A stopcock 301 (see e.g. FIG. 24A) can control the flow of saline.

FIG. 23A illustrates an insertion tube 500 which can be utilized with the introducer sheath 300 to enable a larger dimensioned delivery instrument and larger dimensioned elongated member 12 to be inserted through the introducer sheath 300. Insertion tube 500 has a head portion 502 and an elongated tubular portion 504 extending from head portion 502. A lumen 506 extends through the tube 500. As shown in FIG. 23B, insertion tube 500 is inserted through the valve 308 and into the lumen 309 of introducer sheath 300. The tube 500 terminates proximal of the reduced lumen area 307 of sheath 300. Tube 500 steps down to a smaller internal lumen diameter at region 509.

The lumen 506 of insertion tube 500 preferably has a diameter of about 0.096 inches and can preferably step down to about 0.088 inches (region 509). The lumen 309 of the introducer sheath 300 preferably has a diameter of about 0.125 inches and the reduced lumen area 307 preferably has a diameter D2 of about 0.087 inches, preferably stepped down to a diameter D3 of about 0.079 inches (see FIG. 26C). Preferably, the outer diameter D1 of the introducer sheath 300 is about 0.105 inches and the outer diameter of the tubular portion 504 of the insertion tube 500 is about 0.114 inches. The delivery instrument preferably has an outer diameter of about 0.079 inches. The elongated member 12 preferably has a lengthwise dimension of about 0.313 inches (8 mm). (Note that the foregoing dimensions are provided by way of example and other dimensions are also contemplated.)

Figures 24A, 24B:
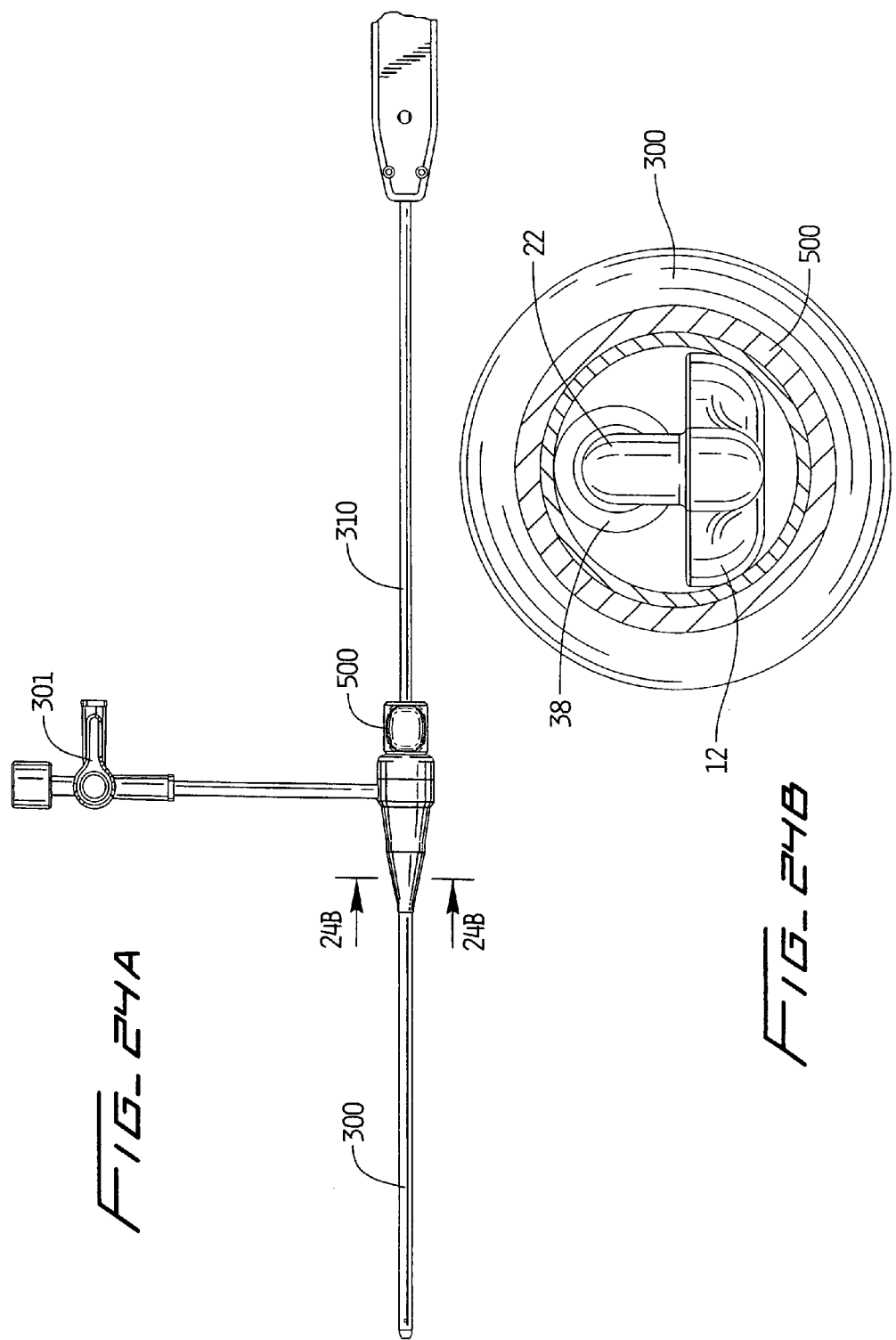
FIG. 24A is a side view of the delivery instrument being inserted into the introducer sheath.
FIG. 24B is a view taken along lines B-B of FIG. 24A showing the sheath and insertion tube in cross-section and the closure device positioned therein.

Due to the use of insertion tube 500, the elongated member 12 can be positioned outside the delivery instrument 310 and fed into the lumen 506 of tube 500 and lumens 309, 307, 305 of the sheath 300. As shown in FIGS. 24-26, when initially inserted, the closure device (collar 38, elongated member 12, etc.) fits within the confines of the sheath 300 without deflecting the sheath wall (FIG. 24B). When the delivery instrument 310 is inserted further into the introducer sheath 500 as shown in FIG. 25A, the sheath wall is deflected as shown in FIG. 25B and is deformed as it is deflected beyond its elastic limit since the internal diameter of the tip is smaller. Full insertion shown in FIG. 26A further deflects (deforms) the wall as shown in FIG. 26B, beyond its elastic limit. Without the use of insertion tube 500, the elongated member 12 would have to be retained within the delivery instrument 310, which would require either a larger diameter delivery instrument 310 or a smaller (lengthwise) elongated member 12.

FIG. 26D illustrates the closure device of FIG. 11B positioned within the introducer sheath 300 to deflect the wall, corresponding to the position of FIG. 26A.

FIGS. 16A-16C illustrate an alternate embodiment of the closure device of the present invention which utilizes a slotted tube to retract and release the closure device. Closure device 150 has an elongated member 152 and clip legs 154a-154d identical to the elongated member 12 and clip legs 30a-30d of closure device 10 of FIG. 1. Closure device 150 also has a collar 158 identical to the collar 38 of FIG. 1. A connecting wire 156, insert molded to elongated member 152 in the same manner as FIG. 11B, connects the clip portion of the device to the elongated member 152. The cross-sectional view of FIG. 16C illustrates how the clip legs 154a-154d and connecting wire 156 are seated within collar 158 along the perimeter to facilitate manufacture.

A slotted tube 160 of the delivery instrument, having a series of slots 162, e.g. four, to create a series of flexible fingers 164 is releasably seated over collar 158 to hold the closure device. Due to this interference fit, when slotted tube 160, which is fixedly mounted to the delivery instrument 161, is pulled proximally with the proximal movement of the delivery instrument, the collar 158, and thus the closure device 150 is pulled proximally to seat the elongated member 152 against the internal wall of the vessel to cover the internal opening of the aperture. When a sufficient load is placed on slotted tube 160, the fingers 164 flex outwardly and slide over the collar 158, thereby releasing the closure device 150 from the slotted tube 160 of the delivery instrument.

In an alternate embodiment (not shown), the release tube, instead of being slotted, has a crimped or swaged tip which is positioned slightly distally of the collar. This tip is flexible so that upon placement of sufficient load on the tube, the tip flexes to ride over the collar to release the closure device. Additionally, dimples could be provided on the interior surface to help retain the tube over the collar, but which would enable release of the collar.

In the alternate embodiment of FIG. 16D, instead of a slotted tube, a pair of jaws 181, 182 are fixed to the delivery instrument 180. Jaws 181, 182 grasp collar 178 of closure device 170. Closure device 170 is substantially identical to device 160 of FIG. 16A having an elongated member 172, a connecting wire 176, collar 178, and four clip legs 174 (only the ends of two are shown for clarity). When a sufficient load is placed on jaws 181, 182, the jaws open and slide off collar 178, thereby releasing the closure device 170 from the jaws of the delivery instrument.

In the embodiment of FIGS. 21 and 22, a pair of jaws 191 of delivery instrument 190 grasps one or more of the clip legs 30. The jaws 191, e.g. an alligator clamp, are spring biased to an open position and are retained by the wall of the introducer sheath 300 in the closed position as shown in FIG. 22. When the delivery instrument is advanced within introducer sheath 300 past the distal tip 302, the jaws 191 move to the open position to release the clip legs and closure device.

FIGS. 31-36 illustrate another alternate embodiment of a delivery instrument for placement of the closure device. Although described for placement of closure device 140 of FIG. 9B, other closure devices described herein can be placed in a similar manner.

Figure 31:
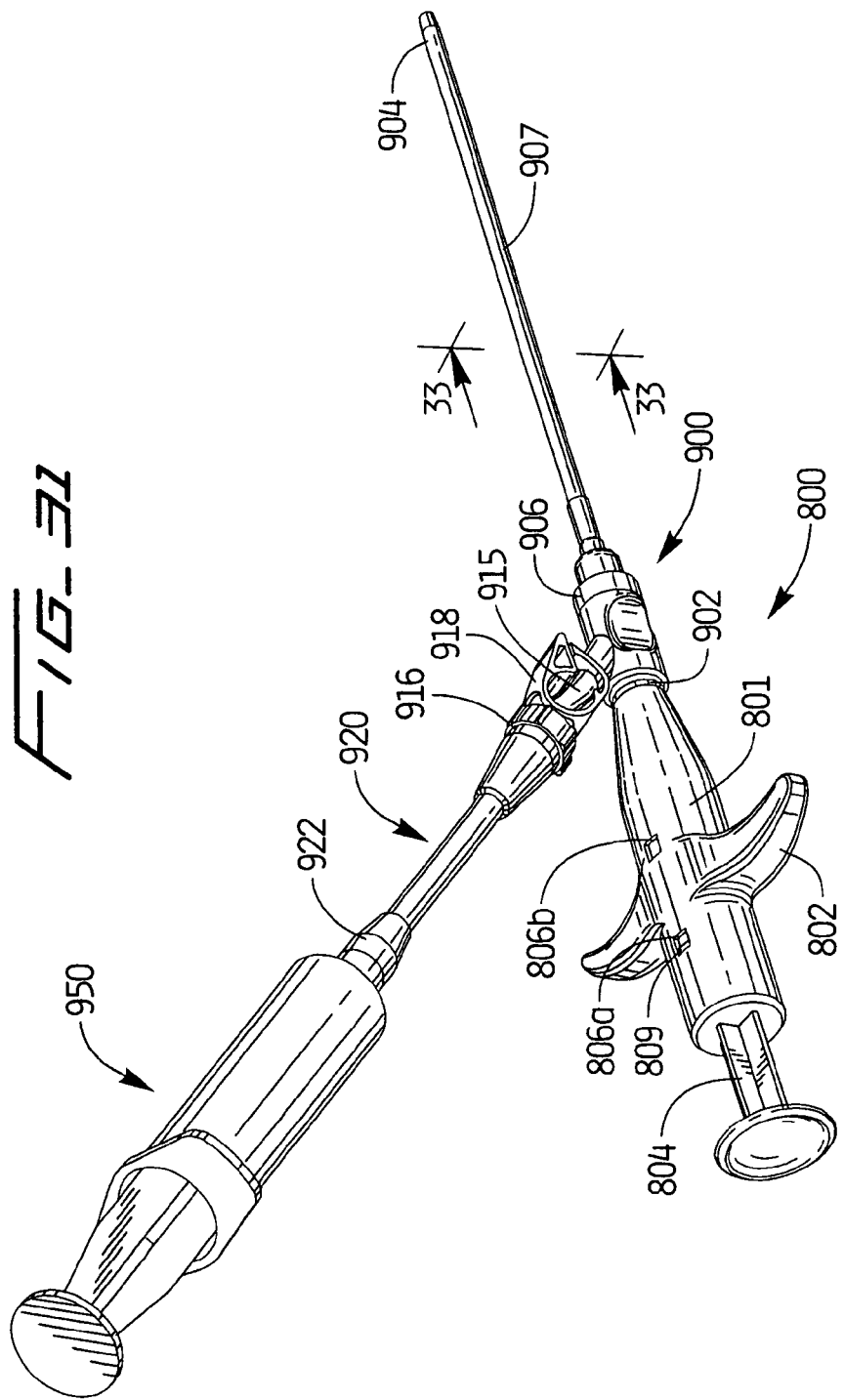
FIG. 31 is a perspective view of another alternate embodiment of the delivery instrument of the present invention for placement of the closure device showing the instrument positioned in an introducer sheath, the plunger in the retracted position, and the syringe connected to the extension assembly.
Figure 34:
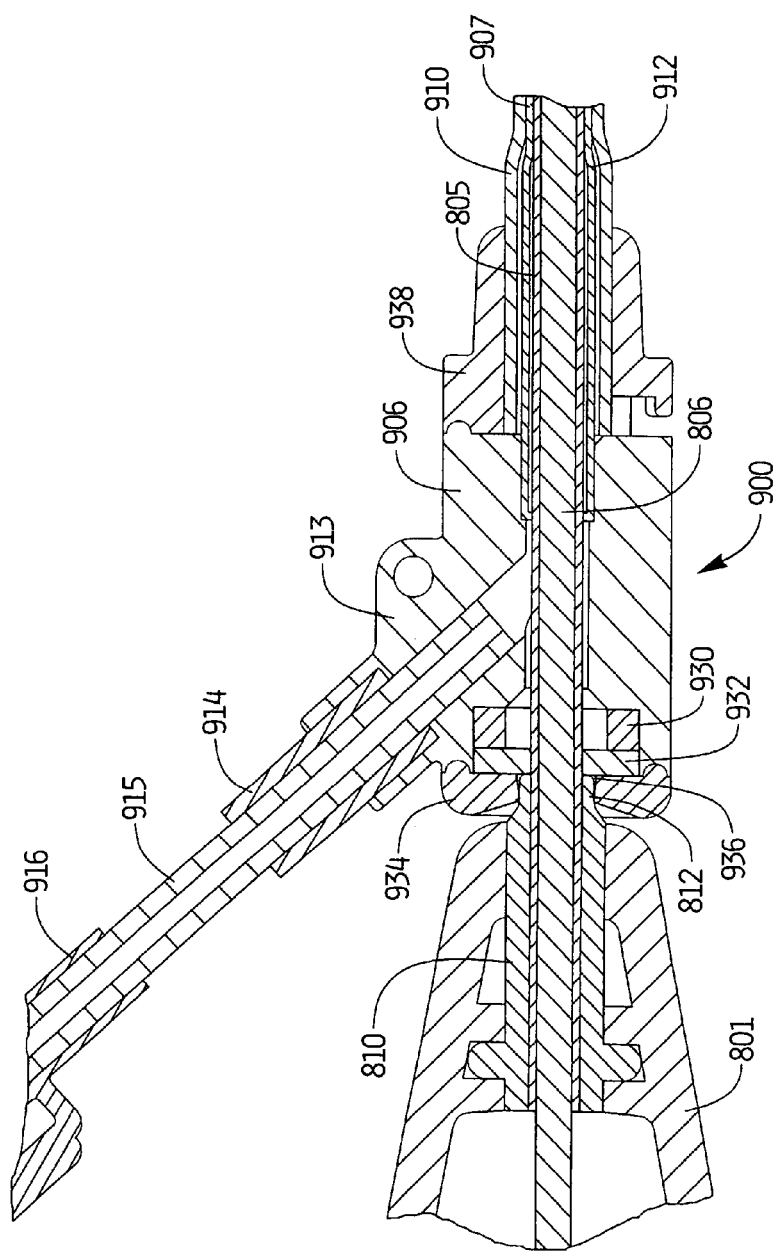
FIG. 34 is a longitudinal sectional view showing a portion of the delivery instrument of FIG. 31 positioned in an introducer sheath.

Turning first to FIG. 31, delivery instrument 800 has a housing 801 having winged grippers 802, a plunger 804 movable axially with respect to housing 801 to advance the closure device 140, and locking windows 806a, 806b to secure the plunger 804 in a retracted and advanced position, respectively. An elongated outer tube 805 extends from housing 801 and is dimensioned to receive the closure device 140 therein. Connected to plunger 804 is a pusher 806 having four longitudinal slots 807 (see FIGS. 33 and 36) to each receive a clip leg in the straightened position within the delivery instrument 800. The distal end of the pusher 806 abuts a region of the clip legs 144 proximal of the retaining collar 148 as shown in FIG. 35.

When the plunger 804 is advanced, the pusher 806 is also moved distally, forcing the closure device 140 forward so that elongated member 142 is advanced into the vessel and moves to its transverse position, helped by the biasing force of offset connecting wire 146 described above. Note that advancement of the plunger 804 moves flexible fingers 809 from engagement in opposed locking windows 806a to engagement in windows 806b to retain the plunger 804 and pusher 806 in the advanced position. Also note the angled surface 809a of fingers 809 enable distal movement of the plunger 804 while straight surface 809b prevents proximal movement out of windows 806a and 806b (see FIG. 32).

The delivery instrument 800 is inserted into the vessel through an introducer sheath, designated by reference numeral 900 in FIGS. 31 and 35. The introducer sheath 900 has a hub 906 with a proximal opening 902 to receive either a conventional dilator or the delivery instrument 800. Sheath tube 907 extends from hub 906 and has an opening 904 in the side wall at the distal end. The distal end is tapered at region 909 to provide a seal with the dilator. The proximal end of the sheath tube 907 is flared at region 912 to enable a smooth transition for the outer tube 805 of the delivery instrument 800 when it is inserted through the introducer sheath 900 because with the closure device 140 in place, the outer tube 805 bulges outwardly. A strain relief 910 surrounds a portion of the sheath tube 907.

The hub 906 of sheath 900 has a 45 degree sidearm 913 having tubing 915, strain relief 914 and a male luer 916 for mounting extension assembly 920. A conventional clamp 918 is placed on tubing 915. The distal end of extension assembly 920 is screwed onto male luer 916 and the proximal end of extension assembly has a mounting assembly 922 with a screw thread for mounting a syringe which is described below.

Hub 906 further includes a valve assembly at the proximal end having a spacer ring 930, a cylindrical valve element 932 having a slit arrangement, and a sheath cap 934. The sheath cap 934 has an opening 936 dimensioned to receive and mount by a snap fit arrangement a dilator (not shown) and the delivery instrument 800. A distal sheath cap 938 is mounted to the distal end of the hub 906. A collar 810 mounted in housing 801 of the delivery instrument 800 and has a snap in tip 812 fitted within the opening 936 in the sheath cap 934.

Placement of the closure device 140 using delivery instrument 800 will now be described. First, to position the introducer sheath 900 in the vessel, a syringe 950, filled with fluid such as saline, is threaded onto proximal threads of extension assembly 920. The introducer sheath 900, with a conventional dilator (not shown) snapped into sheath cap 934, is inserted through the tissue tract over a guidewire toward the vessel wall, with the user attempting to depress the syringe plunger 952. While the sheath 900 is still within the tissue tract, very little saline can be ejected from the syringe 950 through side opening 904. Thus there is little movement of the plunger 952. However, once the introducer sheath 900 is advanced through the tissue tract and through the vessel wall into the vessel lumen, saline can freely flow out through side opening 904 (after flowing in the gap between the dilator and the internal wall of the sheath 900), thus enabling more rapid depression of the plunger 952. This provides a visual and tactile feel that the introducer sheath 900 is desirably positioned within the vessel, thus ensuring that the closure device, when inserted through the sheath 900 via delivery instrument 800, will be inserted into the vessel lumen.

Once the introducer sheath 900 is in place in the vessel, the dilator is removed. The syringe 950 is either filled with cool saline or is detached from the extension assembly 920 and another syringe with cool saline is attached to threads 922. This cool saline is applied to the closure device 140 during delivery to maintain the legs 144 and connecting wire 146 in a cooled martensitic state as described above with respect to other embodiments.

After removal of the dilator, the delivery instrument 800 is ready for insertion through the introducer sheath 900. The closure device 140 is positioned in the delivery instrument 800 as shown in FIG. 35, with the clip legs 142 contained in longitudinal slots of the pusher 806. The elongated member 142 is contained within the confines of the outer tube 805. When inserted through and snapped into the introducer sheath 900, the outer tube 805 remains proximal of the distal tip of the introducer sheath 900 as shown. Next, the plunger 804 is depressed to move the pusher 806 distally (until fingers 809 are positioned in windows 806b) to advance the closure device 140 so the elongated member 142 is moved beyond the confines of the outer tube 805 and beyond the distal tip of the introducer sheath 900. Once outside the confines of tube 805 and sheath 900, the elongated member 142 pivots to a transverse position as shown in FIG. 36.

The sheath 900 and delivery instrument 800 are then pulled proximally, pulling the elongated member 142 against the vessel wall. Once in abutment with the vessel wall, it applies a counterforce against the proximal movement of the sheath 900 and delivery instrument 800. Consequently, subsequent proximal movement of the sheath 900 and instrument 800 will release the clip legs 144 from the confines of the sheath 900 and instrument 800, where the clip legs 144 will return to their curved memorized temperature as they are warmed by body temperature. The sheath 900 and delivery instrument 800 are then removed from the body.

FIGS. 18-20 illustrate alternate embodiments of the delivery instrument which facilitate repositioning of the elongated member within the vessel. That is, in these embodiments, the delivery (closure applying) instrument has a projecting distal tip with an abutment surface configured to engage one of the sides of the elongated member. Pressing of the abutment surface against the top surface of the elongated member forces the elongated member to pivot back to a longitudinal position for withdrawal from the vessel if desired. This more easily allows repositioning within the body prior to deployment of the clip.

More specifically, in FIG. 18, protruding tip 402 of instrument 400 abuts upper surface 99 of elongated member 92. This figure shows use of the closure device 90 of FIG. 11A with the instrument 300. In FIG. 19, closure device 10' is similar to closure device 10' of FIG. 1 (and FIG. 15), except for the separate opening for connecting wire 42'. Elongated member 12' is pivotable back to the position shown in phantom by the projecting tip 412 of instrument 410.

In FIG. 20, the elongated member 102 is biased to a transverse position by the offset suture 104 of closure device 100. It can be pivoted by the projecting tip of the instrument.

FIGS. 17A and 17B show a variation of the elongated member. Closure device 120 has a mushroom shaped saddle 121 which functions to abut the internal wall of the vessel to cover the internal opening of the vessel aperture. The saddle 121 has a circular periphery with two opposing sides 125 curving downwardly. Clip legs 122a, 122b, 122c, and 122d extending from stem 124 function in the same manner as the clip legs described above. Clip legs 122a-122d are shown with penetrating tips 124a-124d, respectively, but non-penetrating tips can also be provided. This closure device 210 is described in more detail in commonly assigned patent application Ser. No. 09/659,648, filed Sep. 12, 2000, the entire contents of which are incorporated herein by reference.

FIGS. 27 and 28 illustrate an alternative embodiment of the closure member of the present invention utilizing a different approach to connecting the clip legs to the elongated member. This version differs from the foregoing embodiments as it eliminates a component to simplify manufacture and simplify the device as a single element can be utilized to both attach the portions of the closure member as well as to bias the elongated member. More specifically, closure device 600 has four legs 602, similar to legs 30 of the embodiment of FIG. 1 in that they have a memorized curved configuration. A tube 604 is preferably welded to elongated member 603, but can be insert molded or attached by other means. Tube 604 is spiral cut to provide flexibility and allow bending of the tube. Extending within the proximal end 606 of the tube 604 are clip legs 602, which are welded through the tube 604 at region 608. Other means of attachment could also be utilized. The proximal portion 606 of tube 604 is not cut to provide rigidity at the region of attachment to clip legs 602. The spiral tube thereby serves several functions: connects the clip legs 602 to the elongated member 603 in a flexible manner, retains the clips legs, and biases the elongated member 603 to a transverse position.

While the above description contains many specifics, those specifics should not be construed as limitations on the scope of the disclosure, but merely as exemplifications of preferred embodiments thereof. For example, any of the foregoing embodiments of the elongated member (patch) could be made of resorbable or non-resorbable material. Moreover, in the foregoing embodiments, the clip portion could be positioned at an acute angle, or other angles, to the elongated member as in FIG. 10J. Additionally, the clip legs of the foregoing embodiments can be positioned in a longitudinal orientation such as in FIG. 10F, a transverse orientation as in FIG. 10J, or another angled orientation with respect to the elongated member, as well as at different angle to the plane of the upper surface of the elongated member. Also, the different configurations of the elongated member disclosed herein can be used with the various clip configurations disclosed in the embodiments described in this application. With suitable materials, the clip portion and elongated member could be a one piece construction. Those skilled in the art will envision many other possible variations that are within the scope and spirit of the disclosure as defined by the claims appended hereto.

What is claimed is:

1. A method for closing an aperture in a vessel wall, the aperture having an external opening in an external region of the vessel wall and an internal opening in an internal region of the vessel wall, the method comprising:

providing a delivery tube having a longitudinal axis, a distal opening and a pusher slidable therein;

providing a closure device having an elongated member having a longitudinal axis and at least two legs proximal of the elongated member, the elongated member and the at least two legs positioned inside the delivery tube so the longitudinal axis of the elongated member is more aligned with the longitudinal axis of the delivery tube than in a placement position and a longitudinal axis of the at least two legs is more aligned with a longitudinal axis of the delivery tube than in a placement position, the elongated member having a length and a width, the length exceeding the width;

inserting the delivery tube through the aperture into the vessel so the distal opening of the delivery tube is within the vessel;

moving the pusher to advance the elongated member through the distal opening of the delivery tube into the vessel;

retracting the delivery tube to pivot the elongated member to a transverse position against the internal opening of the aperture, the elongated member having a dimension at least substantially equal to a dimension of the internal opening of the aperture to prevent egress of fluid through the aperture; and retracting the delivery tube further to release the at least two legs outside the vessel to engage tissue outside the vessel as the legs curve in opposing directions to extend distally toward the elongated member.

2. The method of claim 1, wherein the legs are composed of shape memory material so the step of retracting the delivery tube to release the legs enables the legs to return toward a shape memorized position as they curve in opposing directions.

3. The method of claim 1 wherein the step of providing a closure member having at least two legs includes the step of providing at least two legs formed from a single element of metallic material.

4. The method of claim 3, wherein the at least two legs are composed of shape memory material and the step of releasing the legs allows the legs to return to a curved memorized position.

5. The device of claim 1, wherein the step of releasing the legs allows the legs to curve in a direction substantially parallel to the longitudinal axis of the elongated member.

6. The device of claim 1, wherein the step of releasing the legs allows the legs curve in a direction substantially perpendicular to the longitudinal axis of the elongated member.

7. The device of claim 1, wherein the elongated member is composed of a resorbable material and further comprising the step of leaving the elongated member in the vessel to resorb after a period of time.

8. The method of claim 7, wherein the legs are composed of shape memory material such that retracting the delivery tube to release the legs enables the legs to move to a shape memorized curved position.

9. The method of claim 1, wherein in the delivery position the elongated member is angled and maintains its configuration within the delivery device.

10. The method of claim 9, wherein the step of pulling the elongated member against the vessel pivots the elongated member to a position substantially parallel to the vessel wall.

11. A method for closing an aperture in a vessel wall, the aperture having an external opening in an external region of the vessel wall and an internal opening in an internal region of the vessel wall, the method comprising:

providing a delivery tube and an elongated delivery member having first and second independent longitudinally extending slots;

providing a closure device having an elongated covering member and a first member and a second member;

positioning the elongated covering member in a delivery position so a longitudinal axis of the elongated member is more aligned with a longitudinal axis of the delivery tube than in a placement position;

inserting the delivery tube into the vessel so a distal opening is within the vessel;

exposing the elongated member from the delivery tube;

retracting the delivery tube to move the elongated covering member against the internal opening of the aperture, the elongated covering member having a dimension at least substantially equal to a dimension of the internal opening of the aperture to prevent egress of fluid through the aperture; and subsequently releasing the first member and second member for positioning outside the vessel to retain the elongated covering member.

12. The device of claim 11, wherein the elongated member is composed of a resorbable material and further comprising the step of leaving the elongated member in the vessel to resorb after a period of time.

13. The method of claim 11, wherein the step of pulling the elongated member against the vessel pivots the elongated member to a position substantially parallel to the vessel wall.

14. The method of claim 11, wherein the step of retracting the delivery tube pulls the elongated member into abutment with the vessel wall to apply a counterforce against the proximal movement of the delivery tube.

15. The method of claim 14, wherein subsequent proximal movement of the delivery tube releases the first member due to the counterforce applied by the elongated member.

16. The method of claim 11, wherein a portion of the first member moves toward the elongated covering member subsequent to release of the elongated covering member.

17. The method of claim 11, wherein a portion of the second member moves toward the elongated covering member.

18. The method of claim 11, wherein a suture extends from the elongated covering member and pulling the delivery tube proximally pulls the elongated covering member proximally.

19. The method of claim 18, wherein pulling the delivery tube proximally pulls the suture proximally.

20. The method of claim 19, wherein the suture extends through an opening in the elongated covering member.

* * * * *